US006027882A

United States Patent [19]
Scott et al.

[11] Patent Number: 6,027,882
[45] Date of Patent: *Feb. 22, 2000

[54] PATCHED GENES AND THEIR USE FOR DIAGNOSTICS

[75] Inventors: Matthew P. Scott, Stanford; Lisa V. Goodrich, Palo Alto; Ronald L. Johnson, Redwood City; Ervin Epstein, Orinda; Tony Oro, Palo Alto, all of Calif.

[73] Assignee: The Regents of The University of California

[*] Notice: This patent issued on a continued prosecution application filed under 37 CFR 1.53(d), and is subject to the twenty year patent term provisions of 35 U.S.C. 154(a)(2).

[21] Appl. No.: 08/656,055

[22] Filed: May 31, 1996

Related U.S. Application Data

[63] Continuation-in-part of application No. 08/540,406, Oct. 6, 1995, Pat. No. 5,837,538, which is a continuation-in-part of application No. 08/319,745, Oct. 7, 1994, abandoned.

[51] Int. Cl.[7] .............................. C12P 19/34; C12Q 1/68; C07H 21/02; C07H 21/04
[52] U.S. Cl. .............................. 435/6; 435/91.2; 435/325; 536/23.5; 536/24.31
[58] Field of Search .............................. 435/91.2, 6, 325; 536/23.5, 24.31

[56] References Cited

PUBLICATIONS

Rogers et al., The Journal of Investigative Dermatology Abstracts, vol. 108, No. 4, p. 598, Abstract #364, Apr. 23, 1997.
Hooper and Scott (1989) *Cell* 59:751–765.
Gorlin (1987) *Medicine* 66:98–113.
Habuchi et al. (1995) *Oncogene* 11:1671–1674.
Quinn et al. (1994) *Genes Chromosome Cancer* 11:222–225.
Quinn et al. (1994) *J. Invest. Dermatol.* 102:300–303.
Wicking et al. (1994) *Genomics* 22:505–511.
Roelink et al. (1994) Cell 76:761–775.
Heemskerk and DiNardo (1994) *Cell* 76:449–460.
Tabata and Kornberg (1994) *Cell* 76:89–102.
Krauss et al. (1993) *Cell* 75:1431–1444 (1993).
Nakano et al. (1989) *Nature* 341:508–513.
Riddle et al. (1993) *Cell* 75:1401–1416.
Echelard et al. (1993) *Cell* 75:1417–1430.
Chavrier et al. (1992) *Gene* 112:261–264.
Ma et al. (1992) *Biochemistry* 31:10922–10928.
Thummel et al. (1988) *Gene* 74:445–446.
Simcox et al. (1989) *Development* 107:715–722.
Hidalgo et al. (1990) *Development* 110:291–301.
Philiips et al. (1990) *Development* 110:105–114.
Taylor et al. (1993) *Mechanisms of Develop.* 42:89–96.
Ingham et al. (1991) *Nature* 353:184–187.
Sampedro et al. (1993) *Nature* 353:187–190.

*Primary Examiner*—Bruce R. Campell
*Assistant Examiner*—Jill D. Martin
*Attorney, Agent, or Firm*—Matthew P. Vincent; Beth Arnold; Foley, Hoag & Eliot

[57] ABSTRACT

Methods for isolating patched genes, particularly mammalian patched genes, including mouse and human patched genes, as well as invertebrate patched genes and sequences, are provided. Loss-of function of the patched is associated with the occurrence of human cancers, particularly basal cell carcinomas of the skin. The cancers may be familial, having as a component of risk an inherited genetic predisposition, or may be sporadic. Therefore, methods for using the patched gene as a diagnostic for assessing a genetic predisposition to cancer, and to identify specific cancers having mutations in this gene, are disclosed.

44 Claims, 2 Drawing Sheets

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 736 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
AACNNCNNTN NATGGCACCC CCNCCCAACC TTTNNNCCNN NTAANCAAAA NNCCCCNTTT      60

NATACCCCCT NTAANANTTT TCCACCNNNC NNAAAANNCCN CTGNANACNA NGNAAANCCN    120

TTTTTNAACC CCCCCCACCC GGAATTCCNA NTNNCCNCCC CCAAATTACA ACTCCAGNCC    180

AAAATTNANA NAATTGGTCC TAACCTAACC NATNGTTGTT ACGGTTTCCC CCCCCAAATA    240

CATGCACTGG CCCGAACACT TGATCGTTGC CGTTCCAATA AGAATAAATC TGGTCATATT    300

AAACAAGCCN AAAGCTTTAC AAACTGTTGT ACAATTAATG GGCGAACACG AACTGTTCGA    360

ATTCTGGTCT GGACATTACA AAGTGCACCA CATCGGATGG AACCAGGAGA AGGCCACAAC    420

CGTACTGAAC GCCTGGCAGA AGAAGTTCGC ACAGGTTGGT GGTTGGCGCA AGGAGTAGAG    480

TGAATGGTGG TAATTTTTGG TTGTTCCAGG AGGTGGATCG TCTGACGAAG AGCAAGAAGT    540

CGTCGAATTA CATCTTCGTG ACGTTCTCCA CCGCCAATTT GAACAAGATG TTGAAGGAGG    600

CGTCGAANAC GGACGTGGTG AAGCTGGGGG TGGTGCTGGG GGTGGCGGCG GTGTACGGGT    660

GGGTGGCCCA GTCGGGGCTG GCTGCCTTGG GAGTGCTGGT CTTNGCGNGC TNCNATTCGC    720

CCTATAGTNA GNCGTA                                                    736
```

(2) INFORMATION FOR SEQ ID NO:2:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Xaa Pro Pro Pro Asn Tyr Asn Ser Xaa Pro Lys Xaa Xaa Xaa Leu Val
 1               5                  10                  15

Leu Thr Pro Xaa Val Val Thr Val Ser Pro Lys Tyr Met His Trp
            20                  25                  30

Pro Glu His Leu Ile Val Ala Val Pro Ile Arg Ile Asn Leu Val Ile
        35                  40                  45

Leu Asn Lys Pro Lys Ala Leu Gln Thr Val Val Gln Leu Met Gly Glu
    50                  55                  60

His Glu Leu Phe Glu Phe Trp Ser Gly His Tyr Lys Val His His Ile
65                  70                  75                  80

Gly Trp Asn Gln Glu Lys Ala Thr Thr Val Leu Asn Ala Trp Gln Lys
                85                  90                  95

Lys Phe Ala Gln Val Gly Gly Trp Arg Lys Glu
                100                 105
```

(2) INFORMATION FOR SEQ ID NO:3:

(i) SEQUENCE CHARACTERISTICS:
        (A) LENGTH: 5187 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGGTCTGTCA CCCGGAGCCG GAGTCCCCGG CGGCCAGCAG CGTCCTCGCG AGCCGAGCGC      60

CCAGGCGCGC CCGGAGCCCG CGGCGGCGGC GGCAACATGG CCTCGGCTGG TAACGCCGCC     120

GGGGCCCTGG GCAGGCAGGC CGGCGGCGGG AGGCGCAGAC GGACCGGGGG ACCGCACCGC     180

GCCGCGCCGG ACCGGGACTA TCTGCACCGG CCCAGCTACT GCGACGCCGC CTTCGCTCTG     240

GAGCAGATTT CCAAGGGGAA GGCTACTGGC CGGAAAGCGC CGCTGTGGCT GAGAGCGAAG     300

TTTCAGAGAC TCTTATTTAA ACTGGGTTGT TACATTCAAA AGAACTGCGG CAAGTTTTTG     360

GTTGTGGGTC TCCTCATATT TGGGGCCTTC GCTGTGGGAT TAAAGGCAGC TAATCTCGAG     420

ACCAACGTGG AGGAGCTGTG GGTGGAAGTT GGTGGACGAG TGAGTCGAGA ATTAAATTAT     480

ACCCGTCAGA AGATAGGAGA AGAGGCTATG TTTAATCCTC AACTCATGAT ACAGACTCCA     540

AAAGAAGAAG GCGCTAATGT TCTGACCACA GAGGCTCTCC TGCAACACCT GGACTCAGCA     600

CTCCAGGCCA GTCGTGTGCA CGTCTACATG TATAACAGGC AATGGAAGTT GGAACATTTG     660

TGCTACAAAT CAGGGGAACT TATCACGGAG ACAGGTTACA TGGATCAGAT AATAGAATAC     720

CTTTACCCTT GCTTAATCAT TACACCTTTG GACTGCTTCT GGGAAGGGGC AAAGCTACAG     780

TCCGGGACAG CATACCTCCT AGGTAAGCCT CCTTTACGGT GGACAAACTT TGACCCCTTG     840

GAATTCCTAG AAGAGTTAAA GAAAATAAAC TACCAAGTGG ACAGCTGGGA GGAAATGCTG     900

AATAAAGCCG AAGTTGGCCA TGGGTACATG GACCGGCCTT GCCTCAACCC AGCCGACCCA     960

GATTGCCCTG CCACAGCCCC TAACAAAAAT TCAACCAAAC CTCTTGATGT GGCCCTTGTT    1020

TTGAATGGTG GATGTCAAGG TTTATCCAGG AAGTATATGC ATTGGCAGGA GGAGTTGATT    1080

GTGGGTGGTA CCGTCAAGAA TGCCACTGGA AAACTTGTCA GCGCTCACGC CCTGCAAACC    1140

ATGTTCCAGT TAATGACTCC CAAGCAAATG TATGAACACT TCAGGGGCTA CGACTATGTC    1200

TCTCACATCA ACTGGAATGA AGACAGGGCA GCCGCCATCC TGGAGGCCTG GCAGAGGACT    1260

TACGTGGAGG TGGTTCATCA AAGTGTCGCC CCAAACTCCA CTCAAAAGGT GCTTCCCTTC    1320

ACAACCACGA CCCTGGACGA CATCCTAAAA TCCTTCTCTG ATGTCAGTGT CATCCGAGTG    1380

GCCAGCGGCT ACCTACTGAT GCTTGCCTAT GCCTGTTTAA CCATGCTGCG CTGGGACTGC    1440

TCCAAGTCCC AGGGTGCCGT GGGGCTGGCT GGCGTCCTGT TGGTTGCGCT GTCAGTGGCT    1500

GCAGGATTGG GCCTCTGCTC CTTGATTGGC ATTTCTTTTA ATGCTGCGAC AACTCAGGTT    1560

TTGCCGTTTC TTGCTCTTGG TGTTGGTGTG GATGATGTCT TCCTCCTGGC CCATGCATTC    1620

AGTGAAACAG GACAGAATAA GAGGATTCCA TTTGAGGACA GGACTGGGGA GTGCCTCAAG    1680

CGCACCGGAG CCAGCGTGGC CCTCACCTCC ATCAGCAATG TCACCGCCTT CTTCATGGCC    1740

GCATTGATCC CTATCCCTGC CCTGCGAGCG TTCTCCCTCC AGGCTGCTGT GGTGGTGGTA    1800

TTCAATTTTG CTATGGTTCT GCTCATTTTT CCTGCAATTC TCAGCATGGA TTTATACAGA    1860

CGTGAGGACA GAAGATTGGA TATTTTCTGC TGTTTCACAA GCCCCTGTGT CAGCAGGGTG    1920

ATTCAAGTTG AGCCACAGGC CTACACAGAG CCTCACAGTA ACACCCGGTA CAGCCCCCCA    1980
```

```
CCCCCATACA CCAGCCACAG CTTCGCCCAC GAAACCCATA TCACTATGCA GTCCACCGTT    2040

CAGCTCCGCA CAGAGTATGA CCCTCACACG CACGTGTACT ACACCACCGC CGAGCCACGC    2100

TCTGAGATCT CTGTACAGCC TGTTACCGTC ACCCAGGACA ACCTCAGCTG TCAGAGTCCC    2160

GAGAGCACCA GCTCTACCAG GGACCTGCTC TCCCAGTTCT CAGACTCCAG CCTCCACTGC    2220

CTCGAGCCCC CCTGCACCAA GTGGACACTC TCTTCGTTTG CAGAGAAGCA CTATGCTCCT    2280

TTCCTCCTGA AACCCAAAGC CAAGGTTGTG GTAATCCTTC TTTTCCTGGG CTTGCTGGGG    2340

GTCAGCCTTT ATGGGACCAC CCGAGTGAGA GACGGGCTGG ACCTCACGGA CATTGTTCCC    2400

CGGGAAACCA GAGAATATGA CTTCATAGCT GCCCAGTTCA AGTACTTCTC TTTCTACAAC    2460

ATGTATATAG TCACCCAGAA AGCAGACTAC CCGAATATCC AGCACCTACT TTACGACCTT    2520

CATAAGAGTT TCAGCAATGT GAAGTATGTC ATGCTGGAGG AGAACAAGCA ACTTCCCCAA    2580

ATGTGGCTGC ACTACTTTAG AGACTGGCTT CAAGGACTTC AGGATGCATT TGACAGTGAC    2640

TGGGAAACTG GGAGGATCAT GCCAAACAAT TATAAAAATG GATCAGATGA CGGGGTCCTC    2700

GCTTACAAAC TCCTGGTGCA GACTGGCAGC CGAGACAAGC CCATCGACAT TAGTCAGTTG    2760

ACTAAACAGC GTCTGGTAGA CGCAGATGGC ATCATTAATC CGAGCGCTTT CTACATCTAC    2820

CTGACCGCTT GGGTCAGCAA CGACCCTGTA GCTTACGCTG CCTCCCAGGC CAACATCCGG    2880

CCTCACCGGC CGGAGTGGGT CCATGACAAA GCCGACTACA TGCCAGAGAC CAGGCTGAGA    2940

ATCCCAGCAG CAGAGCCCAT CGAGTACGCT CAGTTCCCTT TCTACCTCAA CGGCCTACGA    3000

GACACCTCAG ACTTTGTGGA AGCCATAGAA AAAGTGAGAG TCATCTGTAA CAACTATACG    3060

AGCCTGGGAC TGTCCAGCTA CCCCAATGGC TACCCCTTCC TGTTCTGGGA GCAATACATC    3120

AGCCTGCGCC ACTGGCTGCT GCTATCCATC AGCGTGGTGC TGGCCTGCAC GTTTCTAGTG    3180

TGCGCAGTCT TCCTCCTGAA CCCCTGGACG GCCGGGATCA TTGTCATGGT CCTGGCTCTG    3240

ATGACCGTTG AGCTCTTTGG CATGATGGGC CTCATTGGGA TCAAGCTGAG TGCTGTGCCT    3300

GTGGTCATCC TGATTGCATC TGTTGGCATC GGAGTGGAGT TCACCGTCCA CGTGGCTTTG    3360

GCCTTTCTGA CAGCCATTGG GGACAAGAAC CACAGGGCTA TGCTCGCTCT GGAACACATG    3420

TTTGCTCCCG TTCTGGACGG TGCTGTGTCC ACTCTGCTGG GTGTACTGAT GCTTGCAGGG    3480

TCCGAATTTG ATTTCATTGT CAGATACTTC TTTGCCGTCC TGGCCATTCT CACCGTCTTG    3540

GGGGTTCTCA ATGGACTGGT TCTGCTGCCT GTCCTCTTAT CCTTCTTTGG ACCGTGTCCT    3600

GAGGTGTCTC CAGCCAATGG CCTAAACCGA CTGCCCACTC CTTCGCCTGA GCCGCCTCCA    3660

AGTGTCGTCC GGTTTGCCGT GCCTCCTGGT CACACGAACA ATGGGTCTGA TTCCTCCGAC    3720

TCGGAGTACA GCTCTCAGAC CACGGTGTCT GGCATCAGTG AGGAGCTCAG GCAATACGAA    3780

GCACAGCAGG GTGCCGGAGG CCCTGCCCAC CAAGTGATTG TGGAAGCCAC AGAAAACCCT    3840

GTCTTTGCCC GGTCCACTGT GGTCCATCCG GACTCCAGAC ATCAGCCTCC CTTGACCCCT    3900

CGGCAACAGC CCCACCTGGA CTCTGGCTCC TTGTCCCCTG GACGGCAAGG CCAGCAGCCT    3960

CGAAGGGATC CCCCTAGAGA AGGCTTGCGG CCACCCCCCT ACAGACCGCG CAGAGACGCT    4020

TTTGAAATTT CTACTGAAGG GCATTCTGGC CCTAGCAATA GGGACCGCTC AGGGCCCCGT    4080

GGGGCCCGTT CTCACAACCC TCGGAACCCA ACGTCCACCG CCATGGGCAG CTCTGTGCCC    4140

AGCTACTGCC AGCCCATCAC CACTGTGACG GCTTCTGCTT CGGTGACTGT TGCTGTGCAT    4200

CCCCCGCCTG GACCTGGGCG CAACCCCCGA GGGGGGCCCT GTCCAGGCTA TGAGAGCTAC    4260

CCTGAGACTG ATCACGGGGT ATTTGAGGAT CCTCATGTGC CTTTTCATGT CAGGTGTGAG    4320
```

```
AGGAGGGACT CAAAGGTGGA GGTCATAGAG CTACAGGACG TGGAATGTGA GGAGAGGCCG    4380

TGGGGGAGCA GCTCCAACTG AGGGTAATTA AAATCTGAAG CAAAGAGGCC AAAGATTGGA    4440

AAGCCCCGCC CCCACCTCTT TCCAGAACTG CTTGAAGAGA ACTGCTTGGA ATTATGGGAA    4500

GGCAGTTCAT TGTTACTGTA ACTGATTGTA TTATTKKGTG AAATATTTCT ATAAATATTT    4560

AARAGGTGTA CACATGTAAT ATACATGGAA ATGCTGTACA GTCTATTTCC TGGGGCCTCT    4620

CCACTCCTGC CCCAGAGTGG GGAGACCACA GGGGCCCTTT CCCCTGTGTA CATTGGTCTC    4680

TGTGCCACAA CCAAGCTTAA CTTAGTTTTA AAAAAAATCT CCCAGCATAT GTCGCTGCTG    4740

CTTAAATATT GTAATTTA CTTGTATAAT TCTATGCAAA TATTGCTTAT GTAATAGGAT     4800

TATTTGTAAA GGTTTCTGTT TAAAATATTT TAAATTTGCA TATCACAACC CTGTGGTAGG   4860

ATGAATTGTT ACTGTTAACT TTTGAACACG CTATGCGTGG TAATTGTTTA ACGAGCAGAC   4920

ATGAAGAAAA CAGGTTAATC CCAGTGGCTT CTCTAGGGGT AGTTGTATAT GGTTCGCATG   4980

GGTGGATGTG TGTGTGCATG TGACTTTCCA ATGTACTGTA TTGTGGTTTG TTGTTGTTGT   5040

TGCTGTTGTT GTTCATTTTG GTGTTTTTGG TTGCTTTGTA TGATCTTAGC TCTGGCCTAG   5100

GTGGGCTGGG AAGGTCCAGG TCTTTTTCTG TCGTGATGCT GGTGGAAAGG TGACCCCAAT   5160

CATCTGTCCT ATTCTCTGGG ACTATTC                                       5187

(2) INFORMATION FOR SEQ ID NO:4:

(i) SEQUENCE CHARACTERISTICS:
        (A) LENGTH: 1311 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Val Ala Pro Asp Ser Glu Ala Pro Ser Asn Pro Arg Ile Thr Ala
1               5                   10                  15

Ala His Glu Ser Pro Cys Ala Thr Glu Ala Arg His Ser Ala Asp Leu
            20                  25                  30

Tyr Ile Arg Thr Ser Trp Val Asp Ala Ala Leu Ala Leu Ser Glu Leu
        35                  40                  45

Glu Lys Gly Asn Ile Glu Gly Gly Arg Thr Ser Leu Trp Ile Arg Ala
    50                  55                  60

Trp Leu Gln Glu Gln Leu Phe Ile Leu Gly Cys Phe Leu Gln Gly Asp
65                  70                  75                  80

Ala Gly Lys Val Leu Phe Val Ala Ile Leu Val Leu Ser Thr Phe Cys
                85                  90                  95

Val Gly Leu Lys Ser Ala Gln Ile His Thr Arg Val Asp Gln Leu Trp
            100                 105                 110

Val Gln Glu Gly Gly Arg Leu Glu Ala Glu Leu Lys Tyr Thr Ala Gln
        115                 120                 125

Ala Leu Gly Glu Ala Asp Ser Ser Thr His Gln Leu Val Ile Gln Thr
    130                 135                 140

Ala Lys Asp Pro Asp Val Ser Leu Leu His Pro Gly Ala Leu Leu Glu
145                 150                 155                 160

His Leu Lys Val Val His Ala Ala Thr Arg Val Thr Val His Met Tyr
                165                 170                 175

Asp Ile Glu Trp Arg Leu Lys Asp Leu Cys Tyr Ser Pro Ser Ile Pro
            180                 185                 190
```

-continued

```
Asp Phe Glu Gly Tyr His His Ile Glu Ser Ile Ile Asp Asn Val Ile
            195                 200                 205
Pro Cys Ala Ile Ile Thr Pro Leu Asp Cys Phe Trp Glu Gly Ser Lys
210                 215                 220
Leu Leu Gly Pro Asp Tyr Pro Ile Tyr Val Pro His Leu Lys His Lys
225                 230                 235                 240
Leu Gln Trp Thr His Leu Asn Pro Leu Glu Val Val Glu Glu Val Lys
            245                 250                 255
Lys Leu Lys Phe Gln Phe Pro Leu Ser Thr Ile Glu Ala Tyr Met Lys
            260                 265                 270
Arg Ala Gly Ile Thr Ser Ala Tyr Met Lys Lys Pro Cys Leu Asp Pro
            275                 280                 285
Thr Asp Pro His Cys Pro Ala Thr Ala Pro Asn Lys Lys Ser Gly His
            290                 295                 300
Ile Pro Asp Val Ala Ala Glu Leu Ser His Gly Cys Tyr Gly Phe Ala
305                 310                 315                 320
Ala Ala Tyr Met His Trp Pro Glu Gln Leu Ile Val Gly Gly Ala Thr
            325                 330                 335
Arg Asn Ser Thr Ser Ala Leu Arg Lys Ala Arg Xaa Leu Gln Thr Val
            340                 345                 350
Val Gln Leu Met Gly Glu Arg Glu Met Tyr Glu Tyr Trp Ala Asp His
            355                 360                 365
Tyr Lys Val His Gln Ile Gly Trp Asn Gln Lys Ala Ala Ala Val
            370                 375                 380
Leu Asp Ala Trp Gln Arg Lys Phe Ala Ala Glu Val Arg Lys Ile Thr
385                 390                 395                 400
Thr Ser Gly Ser Val Ser Ser Ala Tyr Ser Phe Tyr Pro Phe Ser Thr
                    405                 410                 415
Ser Thr Leu Asn Asp Ile Leu Gly Lys Phe Ser Glu Val Ser Leu Lys
                    420                 425                 430
Asn Ile Ile Leu Gly Tyr Met Phe Met Leu Ile Tyr Val Ala Val Thr
            435                 440                 445
Leu Ile Gln Trp Arg Asp Pro Ile Arg Ser Gln Ala Gly Val Gly Ile
450                 455                 460
Ala Gly Val Leu Leu Ser Ile Thr Val Ala Ala Gly Leu Gly Phe
465                 470                 475                 480
Cys Ala Leu Leu Gly Ile Pro Phe Asn Ala Ser Ser Thr Gln Ile Val
            485                 490                 495
Pro Phe Leu Ala Leu Gly Leu Gly Val Gln Asp Met Phe Leu Leu Thr
            500                 505                 510
His Thr Tyr Val Glu Gln Ala Gly Asp Val Pro Arg Glu Glu Arg Thr
            515                 520                 525
Gly Leu Val Leu Lys Lys Ser Gly Leu Ser Val Leu Leu Ala Ser Leu
            530                 535                 540
Cys Asn Val Met Ala Phe Leu Ala Ala Ala Leu Leu Pro Ile Pro Ala
545                 550                 555                 560
Phe Arg Val Phe Cys Leu Gln Ala Ala Ile Leu Leu Leu Phe Asn Leu
            565                 570                 575
Gly Ser Ile Leu Leu Val Phe Pro Ala Met Ile Ser Leu Asp Leu Arg
            580                 585                 590
Arg Arg Ser Ala Ala Arg Ala Asp Leu Leu Cys Cys Leu Met Pro Glu
            595                 600                 605
Ser Pro Leu Pro Lys Lys Lys Ile Pro Glu Arg Ala Lys Thr Arg Lys
```

```
        610                 615                 620
Asn Asp Lys Thr His Arg Ile Asp Thr Thr Arg Gln Pro Leu Asp Pro
625                 630                 635                 640
Asp Val Ser Glu Asn Val Thr Lys Thr Cys Cys Leu Ser Val Ser Leu
                645                 650                 655
Thr Lys Trp Ala Lys Asn Gln Tyr Ala Pro Phe Ile Met Arg Pro Ala
            660                 665                 670
Val Lys Val Thr Ser Met Leu Ala Leu Ile Ala Val Ile Leu Thr Ser
        675                 680                 685
Val Trp Gly Ala Thr Lys Val Lys Asp Gly Leu Asp Leu Thr Asp Ile
690                 695                 700
Val Pro Glu Asn Thr Asp Glu His Glu Phe Leu Ser Arg Gln Glu Lys
705                 710                 715                 720
Tyr Phe Gly Phe Tyr Asn Met Tyr Ala Val Thr Gln Gly Asn Phe Glu
                725                 730                 735
Tyr Pro Thr Asn Gln Lys Leu Leu Tyr Glu Tyr His Asp Gln Phe Val
            740                 745                 750
Arg Ile Pro Asn Ile Ile Lys Asn Asp Asn Gly Gly Leu Thr Lys Phe
        755                 760                 765
Trp Leu Ser Leu Phe Arg Asp Trp Leu Leu Asp Leu Gln Val Ala Phe
770                 775                 780
Asp Lys Glu Val Ala Ser Gly Cys Ile Thr Gln Glu Tyr Trp Cys Lys
785                 790                 795                 800
Asn Ala Ser Asp Glu Gly Ile Leu Ala Tyr Lys Leu Met Val Gln Thr
                805                 810                 815
Gly His Val Asp Asn Pro Ile Asp Lys Ser Leu Ile Thr Ala Gly His
            820                 825                 830
Arg Leu Val Asp Lys Asp Gly Ile Ile Asn Pro Lys Ala Phe Tyr Asn
        835                 840                 845
Tyr Leu Ser Ala Trp Ala Thr Asn Asp Ala Leu Ala Tyr Gly Ala Ser
850                 855                 860
Gln Gly Asn Leu Lys Pro Gln Pro Gln Arg Trp Ile His Ser Pro Glu
865                 870                 875                 880
Asp Val His Leu Glu Ile Lys Lys Ser Ser Pro Leu Ile Tyr Thr Gln
                885                 890                 895
Leu Pro Phe Tyr Leu Ser Gly Leu Ser Asp Thr Xaa Ser Ile Lys Thr
            900                 905                 910
Leu Ile Arg Ser Val Arg Asp Leu Cys Leu Lys Tyr Glu Ala Lys Gly
        915                 920                 925
Leu Pro Asn Phe Pro Ser Gly Ile Pro Phe Leu Phe Trp Glu Gln Tyr
930                 935                 940
Leu Tyr Leu Arg Thr Ser Leu Leu Ala Leu Ala Cys Ala Leu Ala
945                 950                 955                 960
Ala Val Phe Ile Ala Val Met Val Leu Leu Asn Ala Trp Ala Ala
                965                 970                 975
Val Leu Val Thr Leu Ala Leu Ala Thr Leu Val Leu Gln Leu Leu Gly
            980                 985                 990
Val Met Ala Leu Leu Gly Val Lys Leu Ser Ala Met Pro Ala Val Leu
        995                 1000                1005
Leu Val Leu Ala Ile Gly Arg Gly Val His Phe Thr Val His Leu Cys
    1010                1015                1020
Leu Gly Phe Val Thr Ser Ile Gly Cys Lys Arg Arg Ala Ser Leu
1025                1030                1035                1040
```

```
Ala Leu Glu Ser Val Leu Ala Pro Val Val His Gly Ala Leu Ala Ala
            1045                1050                1055

Ala Leu Ala Ala Ser Met Leu Ala Ala Ser Glu Cys Gly Phe Val Ala
            1060                1065                1070

Arg Leu Phe Leu Arg Leu Leu Leu Asp Ile Val Phe Leu Gly Leu Ile
            1075                1080                1085

Asp Gly Leu Leu Phe Phe Pro Ile Val Leu Ser Ile Leu Gly Pro Ala
            1090                1095                1100

Ala Glu Val Arg Pro Ile Glu His Pro Glu Arg Leu Ser Thr Pro Ser
1105                1110                1115                1120

Pro Lys Cys Ser Pro Ile His Pro Arg Lys Ser Ser Ser Ser Ser Gly
            1125                1130                1135

Gly Gly Asp Lys Ser Ser Arg Thr Ser Lys Ser Ala Pro Arg Pro Cys
            1140                1145                1150

Ala Pro Ser Leu Thr Thr Ile Thr Glu Glu Pro Ser Ser Trp His Ser
            1155                1160                1165

Ser Ala His Ser Val Gln Ser Ser Met Gln Ser Ile Val Val Gln Pro
            1170                1175                1180

Glu Val Val Val Glu Thr Thr Thr Tyr Asn Gly Ser Asp Ser Ala Ser
1185                1190                1195                1200

Gly Arg Ser Thr Pro Thr Lys Ser Ser His Gly Gly Ala Ile Thr Thr
            1205                1210                1215

Thr Lys Val Thr Ala Thr Ala Asn Ile Lys Val Glu Val Thr Pro
            1220                1225                1230

Ser Asp Arg Lys Ser Arg Arg Ser Tyr His Tyr Tyr Asp Arg Arg
            1235                1240                1245

Asp Arg Asp Glu Asp Arg Asp Arg Asp Arg Glu Arg Asp Arg Asp Arg
1250                1255                1260

Asp Arg Asp Arg Asp Arg Asp Arg Asp Arg Asp Arg Asp Arg Asp Arg
1265                1270                1275                1280

Glu Arg Ser Arg Glu Arg Asp Arg Arg Asp Arg Tyr Arg Asp Glu Arg
            1285                1290                1295

Asp His Arg Ala Ser Pro Arg Glu Lys Arg Gln Arg Phe Trp Thr
            1300                1305                1310

(2) INFORMATION FOR SEQ ID NO:5:

(i) SEQUENCE CHARACTERISTICS:
        (A) LENGTH: 4434 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CGAAACAAGA GAGCGAGTGA GAGTAGGGAG AGCGTCTGTG TTGTGTGTTG AGTGTCGCCC      60

ACGCACACAG GCGCAAAACA GTGCACACAG ACGCCCGCTG GGCAAGAGAG AGTGAGAGAG     120

AGAAACAGCG GCGCGCGCTC GCCTAATGAA GTTGTTGGCC TGGCTGGCGT GCCGCATCCA     180

CGAGATACAG ATACATCTCT CATGGACCGC GACAGCCTCC CACGCGTTCC GGACACACAC     240

GGCGATGTGG TCGATGAGAA ATTATTCTCG GATCTTTACA TACGCACCAG CTGGGTGGAC     300

GCCCAAGTGG CGCTCGATCA GATAGATAAG GGCAAAGCGC GTGGCAGCCG CACGGCGATC     360

TATCTGCGAT CAGTATTCCA GTCCCACCTC GAAACCCTCG GCAGCTCCGT GCAAAAGCAC     420
```

-continued

```
GCGGGCAAGG TGCTATTCGT GGCTATCCTG GTGCTGAGCA CCTTCTGCGT CGGCCTGAAG    480

AGCGCCCAGA TCCACTCCAA GGTGCACCAG CTGTGGATCC AGGAGGGCGG CCGGCTGGAG    540

GCGGAACTGG CCTACACACA GAAGACGATC GGCGAGGACG AGTCGGCCAC GCATCAGCTG    600

CTCATTCAGA CGACCCACGA CCCGAACGCC TCCGTCCTGC ATCCGCAGGC GCTGCTTGCC    660

CACCTGGAGG TCCTGGTCAA GGCCACCGCC GTCAAGGTGC ACCTCTACGA CACCGAATGG    720

GGGCTGCGCG ACATGTGCAA CATGCCGAGC ACGCCCTCCT TCGAGGGCAT CTACTACATC    780

GAGCAGATCC TGCGCCACCT CATTCCGTGC TCGATCATCA CGCCGCTGGA CTGTTTCTGG    840

GAGGGAAGCC AGCTGTTGGG TCCGGAATCA GCGGTCGTTA TACCAGGCCT CAACCAACGA    900

CTCCTGTGGA CCACCCTGAA TCCCGCCTCT GTGATGCAGT ATATGAAACA AAAGATGTCC    960

GAGGAAAAGA TCAGCTTCGA CTTCGAGACC GTGGAGCAGT ACATGAAGCG TGCGGCCATT   1020

GGCAGTGGCT ACATGGAGAA GCCCTGCCTG AACCCACTGA ATCCCAATTG CCCGGACACG   1080

GCACCGAACA GAACAGCAC CCAGCCGCCG GATGTGGGAG CCATCCTGTC CGGAGGCTGC    1140

TACGGTTATG CCGCGAAGCA CATGCACTGG CCGGAGGAGC TGATTGTGGG CGGACGGAAG   1200

AGGAACCGCA GCGGACACTT GAGGAAGGCC CAGGCCCTGC AGTCGGTGGT GCAGCTGATG   1260

ACCGAGAAGG AAATGTACGA CCAGTGGCAG GACAACTACA AGGTGCACCA TCTTGGATGG   1320

ACGCAGGAGA AGGCAGCGGA GGTTTTGAAC GCCTGGCAGC GCAACTTTTC GCGGGAGGTG   1380

GAACAGCTGC TACGTAAACA GTCGAGAATT GCCACCAACT ACGATATCTA CGTGTTCAGC   1440

TCGGCTGCAC TGGATGACAT CCTGGCCAAG TTCTCCCATC CCAGCGCCTT GTCCATTGTC   1500

ATCGGCGTGG CCGTCACCGT TTTGTATGCC TTTTGCACGC TCCTCCGCTG GAGGGACCCC   1560

GTCCGTGGCC AGAGCAGTGT GGGCGTGGCC GGAGTTCTGC TCATGTGCTT CAGTACCGCC   1620

GCCGGATTGG GATTGTCAGC CCTGCTCGGT ATCGTTTTCA ATGCGCTGAC CGCTGCCTAT   1680

GCGGAGAGCA ATCGGCGGGA GCAGACCAAG CTGATTCTCA GAACGCCAG CACCCAGGTG    1740

GTTCCGTTTT TGGCCCTTGG TCTGGGCGTC GATCACATCT TCATAGTGGG ACCGAGCATC   1800

CTGTTCAGTG CCTGCAGCAC CGCAGGATCC TTCTTTGCGG CCGCCTTTAT TCCGGTGCCG   1860

GCTTTGAAGG TATTCTGTCT GCAGGCTGCC ATCGTAATGT GCTCCAATTT GGCAGCGGCT   1920

CTATTGGTTT TTCCGGCCAT GATTTCGTTG GATCTACGGA GACGTACCGC CGGCAGGGCG   1980

GACATCTTCT GCTGCTGTTT TCCGGTGTGG AAGGAACAGC CGAAGGTGGC ACCTCCGGTG   2040

CTGCCGCTGA ACAACAACAA CGGGCGCGGG GCCCGGCATC CGAAGAGCTG CAACAACAAC   2100

AGGGTGCCGC TGCCCGCCCA GAATCCTCTG CTGGAACAGA GGGCAGACAT CCCTGGGAGC   2160

AGTCACTCAC TGGCGTCCTT CTCCCTGGCA ACCTTCGCCT TTCAGCACTA CACTCCCTTC   2220

CTCATGCGCA GCTGGGTGAA GTTCCTGACC GTTATGGGTT TCCTGGCGGC CCTCATATCC   2280

AGCTTGTATG CCTCCACGCG CCTTCAGGAT GGCCTGGACA TTATTGATCT GGTGCCCAAG   2340

GACAGCAACG AGCACAAGTT CCTGGATGCT CAAACTCGGC TCTTTGGCTT CTACAGCATG   2400

TATGCGGTTA CCCAGGGCAA CTTTGAATAT CCCACCCAGC AGCAGTTGCT CAGGGACTAC   2460

CATGATTCCT TTGTGCGGGT GCCACATGTG ATCAAGAATG ATAACGGTGG ACTGCCGGAC   2520

TTCTGGCTGC TGCTCTTCAG CGAGTGGCTG GGTAATCTGC AAAAGATATT CGACGAGGAA   2580

TACCGCGACG GACGGCTGAC CAAGGAGTGC TGGTTCCCAA ACGCCAGCAG CGATGCCATC   2640

CTGGCCTACA AGCTAATCGT GCAAACCGGC CATGTGGACA CCCCGTGGA CAAGGAACTG    2700

GTGCTCACCA ATCGCCTGGT CAACAGCGAT GGCATCATCA CCAACGCGC CTTCTACAAC    2760

TATCTGTCGG CATGGGCCAC CAACGACGTC TTCGCCTACG AGCTTCTCA GGGCAAATTG    2820
```

```
TATCCGGAAC CGCGCCAGTA TTTTCACCAA CCCAACGAGT ACGATCTTAA GATACCCAAG    2880

AGTCTGCCAT TGGTCTACGC TCAGATGCCC TTTTACCTCC ACGGACTAAC AGATACCTCG    2940

CAGATCAAGA CCCTGATAGG TCATATTCGC GACCTGAGCG TCAAGTACGA GGGCTTCGGC    3000

CTGCCCAACT ATCCATCGGG CATTCCCTTC ATCTTCTGGG AGCAGTACAT GACCCTGCGC    3060

TCCTCACTGG CCATGATCCT GGCCTGCGTG CTACTCGCCG CCCTGGTGCT GGTCTCCCTG    3120

CTCCTGCTCT CCGTTTGGGC CGCCGTTCTC GTGATCCTCA GCGTTCTGGC CTCGCTGGCC    3180

CAGATCTTTG GGGCCATGAC TCTGCTGGGC ATCAAACTCT CGGCCATTCC GGCAGTCATA    3240

CTCATCCTCA GCGTGGGCAT GATGCTGTGC TTCAATGTGC TGATATCACT GGGCTTCATG    3300

ACATCCGTTG GCAACCGACA GCGCCGCGTC CAGCTGAGCA TGCAGATGTC CCTGGGACCA    3360

CTTGTCCACG GCATGCTGAC CTCCGGAGTG GCCGTGTTCA TGCTCTCCAC GTCGCCCTTT    3420

GAGTTTGTGA TCCGGCACTT CTGCTGGCTT CTGCTGGTGG TCTTATGCGT TGGCGCCTGC    3480

AACAGCCTTT TGGTGTTCCC CATCCTACTG AGCATGGTGG GACCGGAGGC GGAGCTGGTG    3540

CCGCTGGAGC ATCCAGACCG CATATCCACG CCCTCTCCGC TGCCCGTGCG CAGCAGCAAG    3600

AGATCGGGCA AATCCTATGT GGTGCAGGGA TCGCGATCCT CGCGAGGCAG CTGCCAGAAG    3660

TCGCATCACC ACCACCACAA AGACCTTAAT GATCCATCGC TGACGACGAT CACCGAGGAG    3720

CCGCAGTCGT GGAAGTCCAG CAACTCGTCC ATCCAGATGC CAATGATTG GACCTACCAG    3780

CCGCGGGAAC AGCGACCCGC CTCCTACGCG GCCCCGCCCC CCGCCTATCA CAAGGCCGCC    3840

GCCCAGCAGC ACCACCAGCA TCAGGGCCCG CCCACAACGC CCCCGCCTCC CTTCCCGACG    3900

GCCTATCCGC CGGAGCTGCA GAGCATCGTG GTGCAGCCGG AGGTGACGGT GGAGACGACG    3960

CACTCGGACA GCAACACCAC CAAGGTGACG GCCACGGCCA ACATCAAGGT GGAGCTGGCC    4020

ATGCCCGGCA GGGCGGTGCG CAGCTATAAC TTTACGAGTT AGCACTAGCA CTAGTTCCTG    4080

TAGCTATTAG GACGTATCTT TAGACTCTAG CCTAAGCCGT AACCCTATTT GTATCTGTAA    4140

AATCGATTTG TCCAGCGGGT CTGCTGAGGA TTTCGTTCTC ATGGATTCTC ATGGATTCTC    4200

ATGGATGCTT AAATGGCATG GTAATTGGCA AAATATCAAT TTTTGTGTCT CAAAAAGATG    4260

CATTAGCTTA TGGTTTCAAG ATACATTTTT AAAGAGTCCG CCAGATATTT ATATAAAAAA    4320

AATCCAAAAT CGACGTATCC ATGAAAATTG AAAAGCTAAG CAGACCCGTA TGTATGTATA    4380

TGTGTATGCA TGTTAGTTAA TTTCCCGAAG TCCGGTATTT ATAGCAGCTG CCTT          4434
```

(2) INFORMATION FOR SEQ ID NO:6:

(i) SEQUENCE CHARACTERISTICS:
        (A) LENGTH: 1285 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Asp Arg Asp Ser Leu Pro Arg Val Pro Asp Thr His Gly Asp Val
 1               5                  10                  15

Val Asp Glu Lys Leu Phe Ser Asp Leu Tyr Ile Arg Thr Ser Trp Val
            20                  25                  30

Asp Ala Gln Val Ala Leu Asp Gln Ile Asp Lys Gly Lys Ala Arg Gly
        35                  40                  45

Ser Arg Thr Ala Ile Tyr Leu Arg Ser Val Phe Gln Ser His Leu Glu
    50                  55                  60
```

-continued

```
Thr Leu Gly Ser Ser Val Gln Lys His Ala Gly Lys Val Leu Phe Val
 65                  70                  75                  80

Ala Ile Leu Val Leu Ser Thr Phe Cys Val Gly Leu Lys Ser Ala Gln
                 85                  90                  95

Ile His Ser Lys Val His Gln Leu Trp Ile Gln Glu Gly Arg Leu
                100                 105                 110

Glu Ala Glu Leu Ala Tyr Thr Gln Lys Thr Ile Gly Glu Asp Glu Ser
                115                 120                 125

Ala Thr His Gln Leu Leu Ile Gln Thr Thr His Asp Pro Asn Ala Ser
            130                 135                 140

Val Leu His Pro Gln Ala Leu Leu Ala His Leu Glu Val Leu Val Lys
145                 150                 155                 160

Ala Thr Ala Val Lys Val His Leu Tyr Asp Thr Glu Trp Gly Leu Arg
                165                 170                 175

Asp Met Cys Asn Met Pro Ser Thr Pro Ser Phe Glu Gly Ile Tyr Tyr
            180                 185                 190

Ile Glu Gln Ile Leu Arg His Leu Ile Pro Cys Ser Ile Ile Thr Pro
            195                 200                 205

Leu Asp Cys Phe Trp Glu Gly Ser Gln Leu Leu Gly Pro Glu Ser Ala
            210                 215                 220

Val Val Ile Pro Gly Leu Asn Gln Arg Leu Leu Trp Thr Thr Leu Asn
225                 230                 235                 240

Pro Ala Ser Val Met Gln Tyr Met Lys Gln Lys Met Ser Glu Glu Lys
                245                 250                 255

Ile Ser Phe Asp Phe Glu Thr Val Glu Gln Tyr Met Lys Arg Ala Ala
            260                 265                 270

Ile Gly Ser Gly Tyr Met Glu Lys Pro Cys Leu Asn Pro Leu Asn Pro
            275                 280                 285

Asn Cys Pro Asp Thr Ala Pro Asn Lys Asn Ser Thr Gln Pro Pro Asp
    290                 295                 300

Val Gly Ala Ile Leu Ser Gly Cys Tyr Gly Tyr Ala Ala Lys His
305                 310                 315                 320

Met His Trp Pro Glu Glu Leu Ile Val Gly Gly Arg Lys Arg Asn Arg
                325                 330                 335

Ser Gly His Leu Arg Lys Ala Gln Ala Leu Gln Ser Val Val Gln Leu
                340                 345                 350

Met Thr Glu Lys Glu Met Tyr Asp Gln Trp Gln Asp Asn Tyr Lys Val
            355                 360                 365

His His Leu Gly Trp Thr Gln Glu Lys Ala Ala Glu Val Leu Asn Ala
    370                 375                 380

Trp Gln Arg Asn Phe Ser Arg Glu Val Glu Gln Leu Leu Arg Lys Gln
385                 390                 395                 400

Ser Arg Ile Ala Thr Asn Tyr Asp Ile Tyr Val Phe Ser Ser Ala Ala
                405                 410                 415

Leu Asp Asp Ile Leu Ala Lys Phe Ser His Pro Ser Ala Leu Ser Ile
            420                 425                 430

Val Ile Gly Val Ala Val Thr Val Leu Tyr Ala Phe Cys Thr Leu Leu
            435                 440                 445

Arg Trp Arg Asp Pro Val Arg Gly Gln Ser Ser Val Gly Val Ala Gly
            450                 455                 460

Val Leu Leu Met Cys Phe Ser Thr Ala Ala Gly Leu Gly Leu Ser Ala
465                 470                 475                 480
```

-continued

```
Leu Leu Gly Ile Val Phe Asn Ala Leu Thr Ala Ala Tyr Ala Glu Ser
                485                 490                 495

Asn Arg Arg Glu Gln Thr Lys Leu Ile Leu Lys Asn Ala Ser Thr Gln
            500                 505                 510

Val Val Pro Phe Leu Ala Leu Gly Leu Gly Val Asp His Ile Phe Ile
            515                 520                 525

Val Gly Pro Ser Ile Leu Phe Ser Ala Cys Ser Thr Ala Gly Ser Phe
        530                 535                 540

Phe Ala Ala Ala Phe Ile Pro Val Pro Ala Leu Lys Val Phe Cys Leu
545                 550                 555                 560

Gln Ala Ala Ile Val Met Cys Ser Asn Leu Ala Ala Ala Leu Leu Val
                565                 570                 575

Phe Pro Ala Met Ile Ser Leu Asp Leu Arg Arg Arg Thr Ala Gly Arg
                580                 585                 590

Ala Asp Ile Phe Cys Cys Cys Phe Pro Val Trp Lys Glu Gln Pro Lys
            595                 600                 605

Val Ala Pro Pro Val Leu Pro Leu Asn Asn Asn Gly Arg Gly Ala
            610                 615                 620

Arg His Pro Lys Ser Cys Asn Asn Asn Arg Val Pro Leu Pro Ala Gln
625                 630                 635                 640

Asn Pro Leu Leu Glu Gln Arg Ala Asp Ile Pro Gly Ser Ser His Ser
                645                 650                 655

Leu Ala Ser Phe Ser Leu Ala Thr Phe Ala Phe Gln His Tyr Thr Pro
            660                 665                 670

Phe Leu Met Arg Ser Trp Val Lys Phe Leu Thr Val Met Gly Phe Leu
            675                 680                 685

Ala Ala Leu Ile Ser Ser Leu Tyr Ala Ser Thr Arg Leu Gln Asp Gly
        690                 695                 700

Leu Asp Ile Ile Asp Leu Val Pro Lys Asp Ser Asn Glu His Lys Phe
705                 710                 715                 720

Leu Asp Ala Gln Thr Arg Leu Phe Gly Phe Tyr Ser Met Tyr Ala Val
                725                 730                 735

Thr Gln Gly Asn Phe Glu Tyr Pro Thr Gln Gln Leu Leu Arg Asp
            740                 745                 750

Tyr His Asp Ser Phe Arg Val Pro His Val Ile Lys Asn Asp Asn Gly
            755                 760                 765

Gly Leu Pro Asp Phe Trp Leu Leu Leu Phe Ser Glu Trp Leu Gly Asn
        770                 775                 780

Leu Gln Lys Ile Phe Asp Glu Glu Tyr Arg Asp Gly Arg Leu Thr Lys
785                 790                 795                 800

Glu Cys Trp Phe Pro Asn Ala Ser Ser Asp Ala Ile Leu Ala Tyr Lys
                805                 810                 815

Leu Ile Val Gln Thr Gly His Val Asp Asn Pro Val Asp Lys Glu Leu
                820                 825                 830

Val Leu Thr Asn Arg Leu Val Asn Ser Asp Gly Ile Ile Asn Gln Arg
            835                 840                 845

Ala Phe Tyr Asn Tyr Leu Ser Ala Trp Ala Thr Asn Asp Val Phe Ala
        850                 855                 860

Tyr Gly Ala Ser Gln Gly Lys Leu Tyr Pro Glu Pro Arg Gln Tyr Phe
865                 870                 875                 880

His Gln Pro Asn Glu Tyr Asp Leu Lys Ile Pro Lys Ser Leu Pro Leu
                885                 890                 895

Val Tyr Ala Gln Met Pro Phe Tyr Leu His Gly Leu Thr Asp Thr Ser
```

-continued

```
                    900                 905                 910
Gln Ile Lys Thr Leu Ile Gly His Ile Arg Asp Leu Ser Val Lys Tyr
        915                 920                 925
Glu Gly Phe Gly Leu Pro Asn Tyr Pro Ser Gly Ile Pro Phe Ile Phe
    930                 935                 940
Trp Glu Gln Tyr Met Thr Leu Arg Ser Ser Leu Ala Met Ile Leu Ala
945                 950                 955                 960
Cys Val Leu Leu Ala Ala Leu Val Leu Ser Leu Leu Leu Ser
                965                 970                 975
Val Trp Ala Ala Val Leu Val Ile Leu Ser Val Leu Ala Ser Leu Ala
            980                 985                 990
Gln Ile Phe Gly Ala Met Thr Leu Leu Gly Ile Lys Leu Ser Ala Ile
        995                 1000                1005
Pro Ala Val Ile Leu Ile Leu Ser Val Gly Met Met Leu Cys Phe Asn
    1010                1015                1020
Val Leu Ile Ser Leu Gly Phe Met Thr Ser Val Gly Asn Arg Gln Arg
1025                1030                1035                1040
Arg Val Gln Leu Ser Met Gln Met Ser Leu Gly Pro Leu Val His Gly
                1045                1050                1055
Met Leu Thr Ser Gly Val Ala Val Phe Met Leu Ser Thr Ser Pro Phe
            1060                1065                1070
Glu Phe Val Ile Arg His Phe Cys Trp Leu Leu Val Val Leu Cys
        1075                1080                1085
Val Gly Ala Cys Asn Ser Leu Leu Val Phe Pro Ile Leu Leu Ser Met
    1090                1095                1100
Val Gly Pro Glu Ala Glu Leu Val Pro Leu Glu His Pro Asp Arg Ile
1105                1110                1115                1120
Ser Thr Pro Ser Pro Leu Pro Val Arg Ser Ser Lys Arg Ser Gly Lys
                1125                1130                1135
Ser Tyr Val Val Gln Gly Ser Arg Ser Ser Arg Gly Ser Cys Gln Lys
            1140                1145                1150
Ser His His His His His Lys Asp Leu Asn Asp Pro Ser Leu Thr Thr
        1155                1160                1165
Ile Thr Glu Glu Pro Gln Ser Trp Lys Ser Ser Asn Ser Ser Ile Gln
    1170                1175                1180
Met Pro Asn Asp Trp Thr Tyr Gln Pro Arg Glu Gln Arg Pro Ala Ser
1185                1190                1195                1200
Tyr Ala Ala Pro Pro Pro Ala Tyr His Lys Ala Ala Gln Gln His
                1205                1210                1215
His Gln His Gln Gly Pro Pro Thr Thr Pro Pro Pro Phe Pro Thr
            1220                1225                1230
Ala Tyr Pro Pro Glu Leu Gln Ser Ile Val Gln Pro Glu Val Thr
        1235                1240                1245
Val Glu Thr Thr His Ser Asp Ser Asn Thr Thr Lys Val Thr Ala Thr
    1250                1255                1260
Ala Asn Ile Lys Val Glu Leu Ala Met Pro Gly Arg Ala Val Arg Ser
1265                1270                1275                1280
Tyr Asn Phe Thr Ser
                1285
```

(2) INFORMATION FOR SEQ ID NO:7:

(i) SEQUENCE CHARACTERISTICS:
        (A) LENGTH: 345 base pairs (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:7:

AAGGTCCATC AGCTTTGGAT ACAGGAAGGT GGTTCGCTCG AGCATGAGCT AGCCTACACG    60

CAGAAATCGC TCGGCGAGAT GGACTCCTCC ACGCACCAGC TGCTAATCCA AACNCCCAAA   120

GATATGGACG CCTCGATACT GCACCCGAAC GCGCTACTGA CGCACCTGGA CGTGGTGAAG   180

AAAGCGATCT CGGTGACGGT GCACATGTAC GACATCACGT GGAGNCTCAA GGACATGTGC   240

TACTCGCCCA GCATACCGAG NTTCGATACG CACTTTATCG AGCAGATCTT CGAGAACATC   300

ATACCGTGCG CGATCATCAC GCCGCTGGAT TGCTTTTGGG AGGGA                  345

(2) INFORMATION FOR SEQ ID NO:8:

(i) SEQUENCE CHARACTERISTICS:
          (A) LENGTH: 115 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:8:

Lys Val His Gln Leu Trp Ile Gln Glu Gly Gly Ser Leu Glu His Glu
1               5                  10                  15

Leu Ala Tyr Thr Gln Lys Ser Leu Gly Glu Met Asp Ser Ser Thr His
            20                  25                  30

Gln Leu Leu Ile Gln Thr Pro Lys Asp Met Asp Ala Ser Ile Leu His
        35                  40                  45

Pro Asn Ala Leu Leu Thr His Leu Asp Val Val Lys Lys Ala Ile Ser
    50                  55                  60

Val Thr Val His Met Tyr Asp Ile Thr Trp Xaa Leu Lys Asp Met Cys
65                  70                  75                  80

Tyr Ser Pro Ser Ile Pro Xaa Phe Asp Thr His Phe Ile Glu Gln Ile
                85                  90                  95

Phe Glu Asn Ile Ile Pro Cys Ala Ile Ile Thr Pro Leu Asp Cys Phe
            100                 105                 110

Trp Glu Gly
        115

(2) INFORMATION FOR SEQ ID NO:9:

(i) SEQUENCE CHARACTERISTICS:
          (A) LENGTH: 5187 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:9:

GGGTCTGTCA CCCGGAGCCG GAGTCCCCGG CGGCCAGCAG CGTCCTCGCG AGCCGAGCGC    60

CCAGGCGCGC CCGGAGCCCG CGGCGGCGGC GGCAACATGG CCCTCGGCTG TAACGCCGCC   120

GGGGCCCTGG GCAGGCAGGC CGGCGGCGGG AGGCGCAGAC GGACCGGGGG ACCGCACCGC   180

GCCGCGCCGG ACCGGGACTA TCTGCACCGG CCCAGCTACT GCGACGCCGC CTTCGCTCTG   240

GAGCAGATTT CCAAGGGGAA GGCTACTGGC CGGAAAGCGC CGCTGTGGCT GAGAGCGAAG   300

-continued

```
TTTCAGAGAC TCTTATTTAA ACTGGGTTGT TACATTCAAA AGAACTGCGG CAAGTTTTTG      360
GTTGTGGGTC TCCTCATATT TGGGGCCTTC GCTGTGGGAT TAAAGGCAGC TAATCTCGAG      420
ACCAACGTGG AGGAGCTGTG GGTGGAAGTT GGTGGACGAG TGAGTCGAGA ATTAAATTAT      480
ACCCGTCAGA AGATAGGAGA AGAGGCTATG TTTAATCCTC AACTCATGAT ACAGACTCCA      540
AAAGAAGAAG GCGCTAATGT TCTGACCACA GAGGCTCTCC TGCAACACCT GGACTCAGCA      600
CTCCAGGCCA GTCGTGTGCA CGTCTACATG TATAACAGGC AATGGAAGTT GGAACATTTG      660
TGCTACAAAT CAGGGGAACT TATCACGGAG ACAGGTTACA TGGATCAGAT AATAGAATAC      720
CTTTACCCTT GCTTAATCAT TACACCTTTG GACTGCTTCT GGGAAGGGGC AAAGCTACAG      780
TCCGGGACAG CATACCTCCT AGGTAAGCCT CCTTTACGGT GGACAAACTT TGACCCCTTG      840
GAATTCCTAG AAGAGTTAAA GAAAATAAAC TACCAAGTGG ACAGCTGGGA GGAAATGCTG      900
AATAAAGCCG AAGTTGGCCA TGGGTACATG GACCGGCCTT GCCTCAACCC AGCCGACCCA      960
GATTGCCCTG CCACAGCCCC TAACAAAAAT TCAACCAAAC CTCTTGATGT GGCCCTTGTT     1020
TTGAATGGTG GATGTCAAGG TTTATCCAGG AAGTATATGC ATTGGCAGGA GGAGTTGATT     1080
GTGGGTGGTA CCGTCAAGAA TGCCACTGGA AAACTTGTCA GCGCTCACGC CCTGCAAACC     1140
ATGTTCCAGT TAATGACTCC CAAGCAAATG TATGAACACT TCAGGGGCTA CGACTATGTC     1200
TCTCACATCA ACTGGAATGA AGACAGGGCA GCCGCCATCC TGGAGGCCTG GCAGAGGACT     1260
TACGTGGAGG TGGTTCATCA AAGTGTCGCC CCAAACTCCA CTCAAAAGGT GCTTCCCTTC     1320
ACAACCACGA CCCTGGACGA CATCCTAAAA TCCTTCTCTG ATGTCAGTGT CATCCGAGTG     1380
GCCAGCGGCT ACCTACTGAT GCTTGCCTAT GCCTGTTTAA CCATGCTGCG CTGGGACTGC     1440
TCCAAGTCCC AGGGTGCCGT GGGGCTGGCT GGCGTCCTGT TGGTTGCGCT GTCAGTGGCT     1500
GCAGGATTGG GCCTCTGCTC CTTGATTGGC ATTTCTTTTA ATGCTGCGAC AACTCAGGTT     1560
TTGCCGTTTC TTGCTCTTGG TGTTGGTGTG GATGATGTCT TCCTCCTGGC CCATGCATTC     1620
AGTGAAACAG GACAGAATAA GAGGATTCCA TTTGAGGACA GGACTGGGGA GTGCCTCAAG     1680
CGCACCGGAG CCAGCGTGGC CCTCACCTCC ATCAGCAATG TCACCGCCTT CTTCATGGCC     1740
GCATTGATCC CTATCCCTGC CCTGCGAGCG TTCTCCCTCC AGGCTGCTGT GGTGGTGGTA     1800
TTCAATTTTG CTATGGTTCT GCTCATTTTT CCTGCAATTC TCAGCATGGA TTTATACAGA     1860
CGTGAGGACA GAAGATTGGA TATTTTCTGC TGTTTCACAA GCCCCTGTGT CAGCAGGGTG     1920
ATTCAAGTTG AGCCACAGGC CTACACAGAG CCTCACAGTA ACACCCGGTA CAGCCCCCCA     1980
CCCCCATACA CCAGCCACAG CTTCGCCCAC GAAACCCATA TCACTATGCA GTCCACCGTT     2040
CAGCTCCGCA CAGAGTATGA CCCTCACACG CACGTGTACT ACACCACCGC CGAGCCACGC     2100
TCTGAGATCT CTGTACAGCC TGTTACCGTC ACCCAGGACA ACCTCAGCTG TCAGAGTCCC     2160
GAGAGCACCA GCTCTACCAG GGACCTGCTC TCCCAGTTCT CAGACTCCAG CCTCCACTGC     2220
CTCGAGCCCC CCTGCACCAA GTGGACACTC TCTTCGTTTG CAGAGAAGCA CTATGCTCCT     2280
TTCCTCCTGA AACCCAAAGC CAAGGTTGTG GTAATCCTTC TTTTCCTGGG CTTGCTGGGG     2340
GTCAGCCTTT ATGGGACCAC CCGAGTGAGA GACGGGCTGG ACCTCACGGA CATTGTTCCC     2400
CGGGAAACCA GAGAATATGA CTTCATAGCT GCCCAGTTCA AGTACTTCTC TTTCTACAAC     2460
ATGTATATAG TCACCCAGAA AGCAGACTAC CCGAATATCC AGCACCTACT TTACGACCTT     2520
CATAAGAGTT TCAGCAATGT GAAGTATGTC ATGCTGGAGG AGAACAAGCA ACTTCCCCAA     2580
ATGTGGCTGC ACTACTTTAG AGACTGGCTT CAAGGACTTC AGGATGCATT TGACAGTGAC     2640
```

```
-continued

TGGGAAACTG GGAGGATCAT GCCAAACAAT TATAAAAATG GATCAGATGA CGGGGTCCTC    2700

GCTTACAAAC TCCTGGTGCA GACTGGCAGC CGAGACAAGC CCATCGACAT TAGTCAGTTG    2760

ACTAAACAGC GTCTGGTAGA CGCAGATGGC ATCATTAATC CGAGCGCTTT CTACATCTAC    2820

CTGACCGCTT GGGTCAGCAA CGACCCTGTA GCTTACGCTG CCTCCCAGGC CAACATCCGG    2880

CCTCACCGGC CGGAGTGGGT CCATGACAAA GCCGACTACA TGCCAGAGAC CAGGCTGAGA    2940

ATCCCAGCAG CAGAGCCCAT CGAGTACGCT CAGTTCCCTT TCTACCTCAA CGGCCTACGA    3000

GACACCTCAG ACTTTGTGGA AGCCATAGAA AAAGTGAGAG TCATCTGTAA CAACTATACG    3060

AGCCTGGGAC TGTCCAGCTA CCCCAATGGC TACCCCTTCC TGTTCTGGGA GCAATACATC    3120

AGCCTGCGCC ACTGGCTGCT GCTATCCATC AGCGTGGTGC TGGCCTGCAC GTTTCTAGTG    3180

TGCGCAGTCT TCCTCCTGAA CCCCTGGACG GCCGGGATCA TTGTCATGGT CCTGGCTCTG    3240

ATGACCGTTG AGCTCTTTGG CATGATGGGC CTCATTGGGA TCAAGCTGAG TGCTGTGCCT    3300

GTGGTCATCC TGATTGCATC TGTTGGCATC GGAGTGGAGT TCACCGTCCA CGTGGCTTTG    3360

GCCTTTCTGA CAGCCATTGG GGACAAGAAC ACACAGGGCTA TGCTCGCTCT GGAACACATG    3420

TTTGCTCCCG TTCTGGACGG TGCTGTGTCC ACTCTGCTGG GTGTACTGAT GCTTGCAGGG    3480

TCCGAATTTG ATTTCATTGT CAGATACTTC TTTGCCGTCC TGGCCATTCT CACCGTCTTG    3540

GGGGTTCTCA ATGGACTGGT TCTGCTGCCT GTCCTCTTAT CCTTCTTTGG ACCGTGTCCT    3600

GAGGTGTCTC CAGCCAATGG CCTAAACCGA CTGCCCACTC CTTCGCCTGA GCCGCCTCCA    3660

AGTGTCGTCC GGTTTGCCGT GCCTCCTGGT CACACGAACA ATGGGTCTGA TTCCTCCGAC    3720

TCGGAGTACA GCTCTCAGAC CACGGTGTCT GGCATCAGTG AGGAGCTCAG GCAATACGAA    3780

GCACAGCAGG GTGCCGGAGG CCCTGCCCAC CAAGTGATTG TGGAAGCCAC AGAAAACCCT    3840

GTCTTTGCCC GGTCCACTGT GGTCCATCCG GACTCCAGAC ATCAGCCTCC CTTGACCCCT    3900

CGGCAACAGC CCCACCTGGA CTCTGGCTCC TTGTCCCCTG GACGGCAAGG CCAGCAGCCT    3960

CGAAGGGATC CCCCTAGAGA AGGCTTGCGG CCACCCCCCT ACAGACCGCG CAGAGACGCT    4020

TTTGAAATTT CTACTGAAGG GCATTCTGGC CCTAGCAATA GGGACCGCTC AGGGCCCCGT    4080

GGGGCCCGTT CTCACAACCC TCGGAACCCA ACGTCCACCG CCATGGGCAG CTCTGTGCCC    4140

AGCTACTGCC AGCCCATCAC CACTGTGACG GCTTCTGCTT CGGTGACTGT TGCTGTGCAT    4200

CCCCCGCCTG GACCTGGGCG CAACCCCCGA GGGGGGCCCT GTCCAGGCTA TGAGAGCTAC    4260

CCTGAGACTG ATCACGGGGT ATTTGAGGAT CCTCATGTGC CTTTTCATGT CAGGTGTGAG    4320

AGGAGGGACT CAAAGGTGGA GGTCATAGAG CTACAGGACG TGGAATGTGA GGAGAGGCCG    4380

TGGGGGAGCA GCTCCAACTG AGGGTAATTA AAATCTGAAG CAAAGAGGCC AAAGATTGGA    4440

AAGCCCCGCC CCCACCTCTT TCCAGAACTG CTTGAAGAGA ACTGCTTGGA ATTATGGGAA    4500

GGCAGTTCAT TGTTACTGTA ACTGATTGTA TTATTKKGTG AAATATTTCT ATAAATATTT    4560

AARAGGTGTA CACATGTAAT ATACATGGAA ATGCTGTACA GTCTATTTCC TGGGGCCTCT    4620

CCACTCCTGC CCCAGAGTGG GGAGACCACA GGGGCCCTTT CCCCTGTGTA CATTGGTCTC    4680

TGTGCCACAA CCAAGCTTAA CTTAGTTTTA AAAAAAATCT CCCAGCATAT GTCGCTGCTG    4740

CTTAAATATT GTATAATTTA CTTGTATAAT TCTATGCAAA TATTGCTTAT GTAATAGGAT    4800

TATTTGTAAA GGTTTCTGTT TAAAATATTT TAAATTTGCA TATCACAACC CTGTGGTAGG    4860

ATGAATTGTT ACTGTTAACT TTTGAACACG CTATGCGTGG TAATTGTTTA ACGAGCAGAC    4920

ATGAAGAAAA CAGGTTAATC CCAGTGGCTT CTCTAGGGGT AGTTGTATAT GGTTCGCATG    4980

GGTGGATGTG TGTGTGCATG TGACTTTCCA ATGTACTGTA TTGTGGTTTG TTGTTGTTGT    5040
```

```
TGCTGTTGTT GTTCATTTTG GTGTTTTTGG TTGCTTTGTA TGATCTTAGC TCTGGCCTAG      5100

GTGGGCTGGG AAGGTCCAGG TCTTTTTCTG TCGTGATGCT GGTGGAAAGG TGACCCCAAT      5160

CATCTGTCCT ATTCTCTGGG ACTATTC                                         5187
```

(2) INFORMATION FOR SEQ ID NO:10:

(i) SEQUENCE CHARACTERISTICS:
        (A) LENGTH: 1434 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Met Ala Ser Ala Gly Asn Ala Ala Gly Ala Leu Gly Arg Gln Ala Gly
1               5                   10                  15

Gly Gly Arg Arg Arg Thr Gly Gly Pro His Arg Ala Ala Pro Asp
            20                  25                  30

Arg Asp Tyr Leu His Arg Pro Ser Tyr Cys Asp Ala Ala Phe Ala Leu
        35                  40                  45

Glu Gln Ile Ser Lys Gly Lys Ala Thr Gly Arg Lys Ala Pro Leu Trp
50                  55                  60

Leu Arg Ala Lys Phe Gln Arg Leu Leu Phe Lys Leu Gly Cys Tyr Ile
65                  70                  75                  80

Gln Lys Asn Cys Gly Lys Phe Leu Val Val Gly Leu Leu Ile Phe Gly
                85                  90                  95

Ala Phe Ala Val Gly Leu Lys Ala Ala Asn Leu Glu Thr Asn Val Glu
            100                 105                 110

Glu Leu Trp Val Glu Val Gly Gly Arg Val Ser Arg Glu Leu Asn Tyr
        115                 120                 125

Thr Arg Gln Lys Ile Gly Glu Glu Ala Met Phe Asn Pro Gln Leu Met
130                 135                 140

Ile Gln Thr Pro Lys Glu Glu Gly Ala Asn Val Leu Thr Thr Glu Ala
145                 150                 155                 160

Leu Leu Gln His Leu Asp Ser Ala Leu Gln Ala Ser Arg Val His Val
                165                 170                 175

Tyr Met Tyr Asn Arg Gln Trp Lys Leu Glu His Leu Cys Tyr Lys Ser
            180                 185                 190

Gly Glu Leu Ile Thr Glu Thr Gly Tyr Met Asp Gln Ile Ile Glu Tyr
        195                 200                 205

Leu Tyr Pro Cys Leu Ile Ile Thr Pro Leu Asp Cys Phe Trp Glu Gly
210                 215                 220

Ala Lys Leu Gln Ser Gly Thr Ala Tyr Leu Leu Gly Lys Pro Pro Leu
225                 230                 235                 240

Arg Trp Thr Asn Phe Asp Pro Leu Glu Phe Leu Glu Glu Leu Lys Lys
                245                 250                 255

Ile Asn Tyr Gln Val Asp Ser Trp Glu Met Leu Asn Lys Ala Glu
            260                 265                 270

Val Gly His Gly Tyr Met Asp Arg Pro Cys Leu Asn Pro Ala Asp Pro
        275                 280                 285

Asp Cys Pro Ala Thr Ala Pro Asn Lys Asn Ser Thr Lys Pro Leu Asp
290                 295                 300

Val Ala Leu Val Leu Asn Gly Gly Cys Gln Gly Leu Ser Arg Lys Tyr
305                 310                 315                 320
```

-continued

```
Met His Trp Gln Glu Glu Leu Ile Val Gly Gly Thr Val Lys Asn Ala
            325                 330                 335

Thr Gly Lys Leu Val Ser Ala His Ala Leu Gln Thr Met Phe Gln Leu
            340                 345                 350

Met Thr Pro Lys Gln Met Tyr Glu His Phe Arg Gly Tyr Asp Tyr Val
            355                 360                 365

Ser His Ile Asn Trp Asn Glu Asp Arg Ala Ala Ile Leu Glu Ala
            370                 375             380

Trp Gln Arg Thr Tyr Val Glu Val His Gln Ser Val Ala Pro Asn
385             390                 395                 400

Ser Thr Gln Lys Val Leu Pro Phe Thr Thr Thr Leu Asp Asp Ile
            405                 410                 415

Leu Lys Ser Phe Ser Asp Val Ser Val Ile Arg Val Ala Ser Gly Tyr
            420                 425             430

Leu Leu Met Leu Ala Tyr Ala Cys Leu Thr Met Leu Arg Trp Asp Cys
            435                 440                 445

Ser Lys Ser Gln Gly Ala Val Gly Leu Ala Gly Val Leu Leu Val Ala
            450                 455                 460

Leu Ser Val Ala Ala Gly Leu Gly Leu Cys Ser Leu Ile Gly Ile Ser
465                 470                 475                 480

Phe Asn Ala Ala Thr Thr Gln Val Leu Pro Phe Leu Ala Leu Gly Val
                485                 490                 495

Gly Val Asp Asp Val Phe Leu Leu Ala His Ala Phe Ser Glu Thr Gly
                500                 505                 510

Gln Asn Lys Arg Ile Pro Phe Glu Asp Arg Thr Gly Glu Cys Leu Lys
            515                 520                 525

Arg Thr Gly Ala Ser Val Ala Leu Thr Ser Ile Ser Asn Val Thr Ala
            530                 535                 540

Phe Phe Met Ala Ala Leu Ile Pro Ile Pro Ala Leu Arg Ala Phe Ser
545                 550                 555                 560

Leu Gln Ala Ala Val Val Val Phe Asn Phe Ala Met Val Leu Leu
            565                 570                 575

Ile Phe Pro Ala Ile Leu Ser Met Asp Leu Tyr Arg Arg Glu Asp Arg
            580                 585                 590

Arg Leu Asp Ile Phe Cys Cys Phe Thr Ser Pro Cys Val Ser Arg Val
            595                 600                 605

Ile Gln Val Glu Pro Gln Ala Tyr Thr Glu Pro His Ser Asn Thr Arg
            610                 615                 620

Tyr Ser Pro Pro Pro Tyr Thr Ser His Ser Phe Ala His Glu Thr
625                 630                 635             640

His Ile Thr Met Gln Ser Thr Val Gln Leu Arg Thr Glu Tyr Asp Pro
                645                 650                 655

His Thr His Val Tyr Tyr Thr Thr Ala Glu Pro Arg Ser Glu Ile Ser
            660                 665                 670

Val Gln Pro Val Thr Val Thr Gln Asp Asn Leu Ser Cys Gln Ser Pro
            675                 680                 685

Glu Ser Thr Ser Ser Thr Arg Asp Leu Leu Ser Gln Phe Ser Asp Ser
            690                 695                 700

Ser Leu His Cys Leu Glu Pro Pro Cys Thr Lys Trp Thr Leu Ser Ser
705                 710                 715                 720

Phe Ala Glu Lys His Tyr Ala Pro Phe Leu Leu Lys Pro Lys Ala Lys
                725                 730                 735
```

-continued

```
Val Val Val Ile Leu Leu Phe Leu Gly Leu Leu Gly Val Ser Leu Tyr
            740                 745                 750

Gly Thr Thr Arg Val Arg Asp Gly Leu Asp Leu Thr Asp Ile Val Pro
            755                 760                 765

Arg Glu Thr Arg Glu Tyr Asp Phe Ile Ala Ala Gln Phe Lys Tyr Phe
            770                 775                 780

Ser Phe Tyr Asn Met Tyr Ile Val Thr Gln Lys Ala Asp Tyr Pro Asn
785                 790                 795                 800

Ile Gln His Leu Leu Tyr Asp Leu His Lys Ser Phe Ser Asn Val Lys
                805                 810                 815

Tyr Val Met Leu Glu Glu Asn Lys Gln Leu Pro Gln Met Trp Leu His
                820                 825                 830

Tyr Phe Arg Asp Trp Leu Gln Gly Leu Gln Asp Ala Phe Asp Ser Asp
            835                 840                 845

Trp Glu Thr Gly Arg Ile Met Pro Asn Asn Tyr Lys Asn Gly Ser Asp
850                 855                 860

Asp Gly Val Leu Ala Tyr Lys Leu Leu Val Gln Thr Gly Ser Arg Asp
865                 870                 875                 880

Lys Pro Ile Asp Ile Ser Gln Leu Thr Lys Gln Arg Leu Val Asp Ala
                885                 890                 895

Asp Gly Ile Ile Asn Pro Ser Ala Phe Tyr Ile Tyr Leu Thr Ala Trp
                900                 905                 910

Val Ser Asn Asp Pro Val Ala Tyr Ala Ala Ser Gln Ala Asn Ile Arg
            915                 920                 925

Pro His Arg Pro Glu Trp Val His Asp Lys Ala Asp Tyr Met Pro Glu
            930                 935                 940

Thr Arg Leu Arg Ile Pro Ala Ala Glu Pro Ile Glu Tyr Ala Gln Phe
945                 950                 955                 960

Pro Phe Tyr Leu Asn Gly Leu Arg Asp Thr Ser Asp Phe Val Glu Ala
                965                 970                 975

Ile Glu Lys Val Arg Val Ile Cys Asn Asn Tyr Thr Ser Leu Gly Leu
                980                 985                 990

Ser Ser Tyr Pro Asn Gly Tyr Pro Phe Leu Phe Trp Glu Gln Tyr Ile
            995                 1000                1005

Ser Leu Arg His Trp Leu Leu Leu Ser Ile Ser Val Val Leu Ala Cys
    1010                1015                1020

Thr Phe Leu Val Cys Ala Val Phe Leu Leu Asn Pro Trp Thr Ala Gly
1025                1030                1035                1040

Ile Ile Val Met Val Leu Ala Leu Met Thr Val Glu Leu Phe Gly Met
                1045                1050                1055

Met Gly Leu Ile Gly Ile Lys Leu Ser Ala Val Pro Val Val Ile Leu
            1060                1065                1070

Ile Ala Ser Val Gly Ile Gly Val Glu Phe Thr Val His Val Ala Leu
            1075                1080                1085

Ala Phe Leu Thr Ala Ile Gly Asp Lys Asn His Arg Ala Met Leu Ala
            1090                1095                1100

Leu Glu His Met Phe Ala Pro Val Leu Asp Gly Ala Val Ser Thr Leu
1105                1110                1115                1120

Leu Gly Val Leu Met Leu Ala Gly Ser Glu Phe Asp Phe Ile Val Arg
                1125                1130                1135

Tyr Phe Phe Ala Val Leu Ala Ile Leu Thr Val Leu Gly Val Leu Asn
            1140                1145                1150

Gly Leu Val Leu Leu Pro Val Leu Leu Ser Phe Phe Gly Pro Cys Pro
```

```
            1155                1160                1165
Glu Val Ser Pro Ala Asn Gly Leu Asn Arg Leu Pro Thr Pro Ser Pro
            1170                1175                1180
Glu Pro Pro Pro Ser Val Val Arg Phe Ala Val Pro Pro Gly His Thr
1185                1190                1195                1200
Asn Asn Gly Ser Asp Ser Ser Asp Ser Glu Tyr Ser Ser Gln Thr Thr
            1205                1210                1215
Val Ser Gly Ile Ser Glu Glu Leu Arg Gln Tyr Glu Ala Gln Gln Gly
            1220                1225                1230
Ala Gly Gly Pro Ala His Gln Val Ile Val Glu Ala Thr Glu Asn Pro
            1235                1240                1245
Val Phe Ala Arg Ser Thr Val Val His Pro Asp Ser Arg His Gln Pro
            1250                1255                1260
Pro Leu Thr Pro Arg Gln Gln Pro His Leu Asp Ser Gly Ser Leu Ser
1265                1270                1275                1280
Pro Gly Arg Gln Gly Gln Gln Pro Arg Arg Asp Pro Pro Arg Glu Gly
            1285                1290                1295
Leu Arg Pro Pro Pro Tyr Arg Pro Arg Arg Asp Ala Phe Glu Ile Ser
            1300                1305                1310
Thr Glu Gly His Ser Gly Pro Ser Asn Arg Asp Arg Ser Gly Pro Arg
            1315                1320                1325
Gly Ala Arg Ser His Asn Pro Arg Asn Pro Thr Ser Thr Ala Met Gly
            1330                1335                1340
Ser Ser Val Pro Ser Tyr Cys Gln Pro Ile Thr Thr Val Thr Ala Ser
1345                1350                1355                1360
Ala Ser Val Thr Val Ala Val His Pro Pro Gly Pro Gly Arg Asn
            1365                1370                1375
Pro Arg Gly Gly Pro Cys Pro Gly Tyr Glu Ser Tyr Pro Glu Thr Asp
            1380                1385                1390
His Gly Val Phe Glu Asp Pro His Val Pro Phe His Val Arg Cys Glu
            1395                1400                1405
Arg Arg Asp Ser Lys Val Glu Val Ile Glu Leu Gln Asp Val Glu Cys
            1410                1415                1420
Glu Glu Arg Pro Trp Gly Ser Ser Ser Asn
1425                1430

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Ile Ile Thr Pro Leu Asp Cys Phe Trp Glu Gly
1                 5                  10

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO:12:

Leu Ile Val Gly Gly
1               5

(2) INFORMATION FOR SEQ ID NO:13:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:13:

Pro Phe Phe Trp Glu Gln Tyr
1               5

(2) INFORMATION FOR SEQ ID NO:14:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:14:

GGACGAATTC AARGTNCAYC ARYTNTGG                                       28

(2) INFORMATION FOR SEQ ID NO:15:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:15:

GGACGAATTC CYTCCCARAA RCANTC                                         26

(2) INFORMATION FOR SEQ ID NO:16:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO:16:

GGACGAATTC YTNGANTGYT TYTGGGA                                        27

(2) INFORMATION FOR SEQ ID NO:17:

(i) SEQUENCE CHARACTERISTICS:
       (A) LENGTH: 31 base pairs
       (B) TYPE: nucleic acid
       (C) STRANDEDNESS: single
       (D) TOPOLOGY: linear

```
    (ii) MOLECULE TYPE: other nucleic acid
         (A) DESCRIPTION: /desc = "primer"

(xi) SEQUENCE DESCRIPTION: SEQ ID NO:17:

CATACCAGCC AAGCTTGTCN GGCCARTGCA T                                         31

(2) INFORMATION FOR SEQ ID NO:18:

(i) SEQUENCE CHARACTERISTICS:
        (A) LENGTH: 5288 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GAATTCCGGG GACCGCAAGG AGTGCCGCGG AAGCGCCCGA AGGACAGGCT CGCTCGGCGC           60

GCCGGCTCTC GCTCTTCCGC GAACTGGATG TGGGCAGCGG CGGCCGCAGA GACCTCGGGA         120

CCCCCGCGCA ATGTGGCAAT GGAAGGCGCA GGGTCTGACT CCCCGGCAGC GGCCGCGGCC         180

GCAGCGGCAG CAGCGCCCGC CGTGTGAGCA GCAGCAGCGG CTGGTCTGTC AACCGGAGCC         240

CGAGCCCGAG CAGCCTGCGG CCAGCAGCGT CCTCGCAAGC CGAGCGCCCA GGCGCGCCAG         300

GAGCCCGCAG CAGCGGCAGC AGCGCGCCGG GCCGCCCGGG AAGCCTCCGT CCCCGCGGCG         360

GCGGCGGCGG CGGCGGCGGC AACATGGCCT CGGCTGGTAA CGCCGCCGAG CCCCAGGACC         420

GCGGCGGCGG CGGCAGCGGC TGTATCGGTG CCCCGGGACG GCCGGCTGGA GGCGGGAGGC         480

GCAGACGGAC GGGGGGGCTG CGCCGTGCTG CCGCGCCGGA CCGGGACTAT CTGCACCGGC         540

CCAGCTACTG CGACGCCGCC TTCGCTCTGG AGCAGATTTC CAAGGGGAAG GCTACTGGCC         600

GGAAAGCGCC ACTGTGGCTG AGAGCGAAGT TCAGAGACT CTTATTTAAA CTGGGTTGTT          660

ACATTCAAAA AAACTGCGGC AAGTTCTTGG TTGTGGGCCT CCTCATATTT GGGGCCTTCG         720

CGGTGGGATT AAAAGCAGCG AACCTCGAGA CCAACGTGGA GGAGCTGTGG GTGGAAGTTG         780

GAGGACGAGT AAGTCGTGAA TTAAATTATA CTCGCCAGAA GATTGGAGAA GAGGCTATGT         840

TTAATCCTCA ACTCATGATA CAGACCCCTA AGAAGAAGG TGCTAATGTC CTGACCACAG          900

AAGCGCTCCT ACAACACCTG GACTCGGCAC TCCAGGCCAG CCGTGTCCAT GTATACATGT         960

ACAACAGGCA GTGGAAATTG AACATTTGT GTTACAAATC AGGAGAGCTT ATCACAGAAA         1020

CAGGTTACAT GGATCAGATA ATAGAATATC TTTACCCTTG TTTGATTATT ACACCTTTGG        1080

ACTGCTTCTG GGAAGGGGCG AAATTACAGT CTGGGACAGC ATACCTCCTA GGTAAACCTC        1140

CTTTGCGGTG GACAAACTTC GACCCTTTGG AATTCCTGGA AGAGTTAAAG AAAATAAACT        1200

ATCAAGTGGA CAGCTGGGAG GAAATGCTGA ATAAGGCTGA GGTTGGTCAT GGTTACATGG        1260

ACCGCCCCTG CCTCAATCCG GCCGATCCAG ACTGCCCCGC CACAGCCCCC AACAAAAATT        1320

CAACCAAACC TCTTGATATG GCCCTTGTTT TGAATGGTGG ATGTCATGGC TTATCCAGAA        1380

AGTATATGCA CTGGCAGGAG GAGTTGATTG TGGGTGGCAC AGTCAAGAAC AGCACTGGAA        1440

AACTCGTCAG CGCCCATGCC CTGCAGACCA TGTTCCAGTT AATGACTCCC AAGCAAATGT        1500

ACGAGCACTT CAAGGGGTAC GAGTATGTCT CACACATCAA CTGGAACGAG ACAAAGCGG         1560

CAGCCATCCT GGAGGCCTGG CAGAGGACAT ATGTGGAGGT GGTTCATCAG AGTGTCGCAC        1620

AGAACTCCAC TCAAAAGGTG CTTTCCTTCA CCACCACGAC CCTGGACGAC ATCCTGAAAT        1680

CCTTCTCTGA CGTCAGTGTC ATCCGCGTGG CCAGCGGCTA CTTACTCATG CTCGCCTATG        1740

CCTGTCTAAC CATGCTGCGC TGGGACTGCT CCAAGTCCCA GGGTGCCGTG GGGCTGGCTG        1800
```

```
GCGTCCTGCT GGTTGCACTG TCAGTGGCTG CAGGACTGGG CCTGTGCTCA TTGATCGGAA    1860

TTTCCTTTAA CGCTGCAACA ACTCAGGTTT TGCCATTTCT CGCTCTTGGT GTTGGTGTGG    1920

ATGATGTTTT TCTTCTGGCC CACGCCTTCA GTGAAACAGG ACAGAATAAA AGAATCCCTT    1980

TTGAGGACAG GACCGGGGAG TGCCTGAAGC GCACAGGAGC CAGCGTGGCC CTCACGTCCA    2040

TCAGCAATGT CACAGCCTTC TTCATGGCCG CGTTAATCCC AATTCCCGCT CTGCGGGCGT    2100

TCTCCCTCCA GGCAGCGGTA GTAGTGGTGT TCAATTTTGC CATGGTTCTG CTCATTTTTC    2160

CTGCAATTCT CAGCATGGAT TTATATCGAC GCGAGGACAG GAGACTGGAT ATTTTCTGCT    2220

GTTTTACAAG CCCCTGCGTC AGCAGAGTGA TTCAGGTTGA ACCTCAGGCC TACACCGACA    2280

CACACGACAA TACCCGCTAC AGCCCCCCAC CTCCCTACAG CAGCCACAGC TTTGCCCATG    2340

AAACGCAGAT TACCATGCAG TCCACTGTCC AGCTCCGCAC GGAGTACGAC CCCCACACGC    2400

ACGTGTACTA CACCACCGCT GAGCCGCGCT CCGAGATCTC TGTGCAGCCC GTCACCGTGA    2460

CACAGGACAC CCTCAGCTGC CAGAGCCCAG AGAGCACCAG CTCCACAAGG GACCTGCTCT    2520

CCCAGTTCTC CGACTCCAGC CTCCACTGCC TCGAGCCCCC CTGTACGAAG TGGACACTCT    2580

CATCTTTTGC TGAGAAGCAC TATGCTCCTT TCCTCTTGAA ACCAAAAGCC AAGGTAGTGG    2640

TGATCTTCCT TTTTCTGGGC TTGCTGGGGG TCAGCCTTTA TGGCACCACC CGAGTGAGAG    2700

ACGGGCTGGA CCTTACGGAC ATTGTACCTC GGGAAACCAG AGAATATGAC TTTATTGCTG    2760

CACAATTCAA ATACTTTTCT TTCTACAACA TGTATATAGT CACCCAGAAA GCAGACTACC    2820

CGAATATCCA GCACTTACTT TACGACCTAC ACAGGAGTTT CAGTAACGTG AAGTATGTCA    2880

TGTTGGAAGA AAACAAACAG CTTCCCAAAA TGTGGCTGCA CTACTTCAGA GACTGGCTTC    2940

AGGGACTTCA GGATGCATTT GACAGTGACT GGGAAACCGG GAAAATCATG CCAAACAATT    3000

ACAAGAATGG ATCAGACGAT GGAGTCCTTG CCTACAAACT CCTGGTGCAA ACCGGCAGCC    3060

GCGATAAGCC CATCGACATC AGCCAGTTGA CTAAACAGCG TCTGGTGGAT GCAGATGGCA    3120

TCATTAATCC CAGCGCTTTC TACATCTACC TGACGGCTTG GGTCAGCAAC GACCCCGTCG    3180

CGTATGCTGC CTCCCAGGCC AACATCCGGC CACACCGACC AGAATGGGTC CACGACAAAG    3240

CCGACTACAT GCCTGAAACA AGGCTGAGAA TCCCGGCAGC AGAGCCCATC GAGTATGCCC    3300

AGTTCCCTTT CTACCTCAAC GGGTTGCGGG ACACCTCAGA CTTTGTGGAG GCAATTGAAA    3360

AAGTAAGGAC CATCTGCAGC AACTATACGA GCCTGGGGCT GTCCAGTTAC CCCAACGGCT    3420

ACCCCTTCCT CTTCTGGGAG CAGTACATCG GCCTCCGCCA CTGGCTGCTG CTGTTCATCA    3480

GCGTGGTGTT GGCCTGCACA TTCCTCGTGT GCGCTGTCTT CCTTCTGAAC CCCTGGACGG    3540

CCGGGATCAT TGTGATGGTC CTGGCGCTGA TGACGGTCGA GCTGTTCGGC ATGATGGGCC    3600

TCATCGGAAT CAAGCTCAGT GCCGTGCCCG TGGTCATCCT GATCGCTTCT GTTGGCATAG    3660

GAGTGGAGTT CACCGTTCAC GTTGCTTTGG CCTTTCTGAC GGCCATCGGC GACAAGAACC    3720

GCAGGGCTGT GCTTGCCCTG GAGCACATGT TTGCACCCGT CCTGGATGGC GCCGTGTCCA    3780

CTCTGCTGGG AGTGCTGATG CTGGCGGGAT CTGAGTTCGA CTTCATTGTC AGGTATTTCT    3840

TTGCTGTGCT GGCGATCCTC ACCATCCTCG GCGTTCTCAA TGGGCTGGTT TTGCTTCCCG    3900

TGCTTTTGTC TTTCTTTGGA CCATATCCTG AGGTGTCTCC AGCCAACGGC TTGAACCGCC    3960

TGCCCACACC CTCCCCTGAG CCACCCCCCA GCGTGGTCCG CTTCGCCATG CCGCCCGGCC    4020

ACACGCACAG CGGGTCTGAT TCCTCCGACT CGGAGTATAG TTCCCAGACG ACAGTGTCAG    4080

GCCTCAGCGA GGAGCTTCGG CACTACGAGG CCCAGCAGGG CGCGGGAGGC CCTGCCCACC    4140
```

-continued

```
AAGTGATCGT GGAAGCCACA GAAAACCCCG TCTTCGCCCA CTCCACTGTG GTCCATCCCG      4200

AATCCAGGCA TCACCCACCC TCGAACCCGA GACAGCAGCC CCACCTGGAC TCAGGGTCCC      4260

TGCCTCCCGG ACGGCAAGGC CAGCAGCCCC GCAGGGACCC CCCCAGAGAA GGCTTGTGGC      4320

CACCCCTCTA CAGACCGCGC AGAGACGCTT TTGAAATTTC TACTGAAGGG CATTCTGGCC      4380

CTAGCAATAG GGCCCGCTGG GGCCCTCGCG GGGCCCGTTC TCACAACCCT CGGAACCCAG      4440

CGTCCACTGC CATGGGCAGC TCCGTGCCCG GCTACTGCCA GCCCATCACC ACTGTGACGG      4500

CTTCTGCCTC CGTGACTGTC GCCGTGCACC CGCCGCCTGT CCCTGGGCCT GGGCGGAACC      4560

CCCGAGGGGG ACTCTGCCCA GGCTACCCTG AGACTGACCA CGGCCTGTTT GAGGACCCCC      4620

ACGTGCCTTT CCACGTCCGG TGTGAGAGGA GGGATTCGAA GGTGGAAGTC ATTGAGCTGC      4680

AGGACGTGGA ATGCGAGGAG AGGCCCCGGG GAAGCAGCTC CAACTGAGGG TGATTAAAAT      4740

CTGAAGCAAA GAGGCCAAAG ATTGGAAACC CCCCACCCCC ACCTCTTTCC AGAACTGCTT      4800

GAAGAGAACT GGTTGGAGTT ATGGAAAAGA TGCCCTGTGC CAGGACAGCA GTTCATTGTT      4860

ACTGTAACCG ATTGTATTAT TTTGTTAAAT ATTTCTATAA ATATTTAAGA GATGTACACA      4920

TGTGTAATAT AGGAAGGAAG GATGTAAAGT GGTATGATCT GGGGCTTCTC CACTCCTGCC      4980

CCAGAGTGTG GAGGCCACAG TGGGGCCTCT CCGTATTTGT GCATTGGGCT CCGTGCCACA      5040

ACCAAGCTTC ATTAGTCTTA AATTTCAGCA TATGTTGCTG CTGCTTAAAT ATTGTATAAT      5100

TTACTTGTAT AATTCTATGC AAATATTGCT TATGTAATAG GATTATTTTG TAAAGGTTTC      5160

TGTTTAAAAT ATTTTAAATT TGCATATCAC AACCCTGTGG TAGTATGAAA TGTTACTGTT      5220

AACTTTCAAA CACGCTATGC GTGATAATTT TTTTGTTTAA TGAGCAGATA TGAAGAAAGC      5280

CCGGAATT                                                              5288
```

(2) INFORMATION FOR SEQ ID NO:19:

(i) SEQUENCE CHARACTERISTICS:
    (A) LENGTH: 1447 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:19:

```
Met Ala Ser Ala Gly Asn Ala Ala Glu Pro Gln Asp Arg Gly Gly
1               5                   10                  15

Gly Ser Gly Cys Ile Gly Ala Pro Gly Arg Pro Ala Gly Gly Gly Arg
                20                  25                  30

Arg Arg Arg Thr Gly Gly Leu Arg Arg Ala Ala Pro Asp Arg Asp
            35                  40                  45

Tyr Leu His Arg Pro Ser Tyr Cys Asp Ala Ala Phe Ala Leu Glu Gln
    50                  55                  60

Ile Ser Lys Gly Lys Ala Thr Gly Arg Lys Ala Pro Leu Trp Leu Arg
65                  70                  75                  80

Ala Lys Phe Gln Arg Leu Leu Phe Lys Leu Gly Cys Tyr Ile Gln Lys
                85                  90                  95

Asn Cys Gly Lys Phe Leu Val Val Gly Leu Leu Ile Phe Gly Ala Phe
            100                 105                 110

Ala Val Gly Leu Lys Ala Ala Asn Leu Glu Thr Asn Val Glu Glu Leu
        115                 120                 125

Trp Val Glu Val Gly Gly Arg Val Ser Arg Glu Leu Asn Tyr Thr Arg
    130                 135                 140
```

-continued

```
Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
            180                 185                 190

Tyr Asn Arg Gln Trp Lys Leu Glu His Leu Cys Tyr Lys Ser Gly Glu
        195                 200                 205

Leu Ile Thr Glu Thr Gly Tyr Met Asp Gln Ile Ile Glu Tyr Leu Tyr
    210                 215                 220

Pro Cys Leu Ile Ile Thr Pro Leu Asp Cys Phe Trp Glu Gly Ala Lys
225                 230                 235                 240

Leu Gln Ser Gly Thr Ala Tyr Leu Leu Gly Lys Pro Leu Arg Trp
                245                 250                 255

Thr Asn Phe Asp Pro Leu Glu Phe Leu Glu Glu Leu Lys Lys Ile Asn
            260                 265                 270

Tyr Gln Val Asp Ser Trp Glu Glu Met Leu Asn Lys Ala Glu Val Gly
        275                 280                 285

His Gly Tyr Met Asp Arg Pro Cys Leu Asn Pro Ala Asp Pro Asp Cys
    290                 295                 300

Pro Ala Thr Ala Pro Asn Lys Asn Ser Thr Lys Pro Leu Asp Met Ala
305                 310                 315                 320

Leu Val Leu Asn Gly Gly Cys His Gly Leu Ser Arg Lys Tyr Met His
                325                 330                 335

Trp Gln Glu Glu Leu Ile Val Gly Gly Thr Val Lys Asn Ser Thr Gly
            340                 345                 350

Lys Leu Val Ser Ala His Ala Leu Gln Thr Met Phe Gln Leu Met Thr
        355                 360                 365

Pro Lys Gln Met Tyr Glu His Phe Lys Gly Tyr Glu Tyr Val Ser His
    370                 375                 380

Ile Asn Trp Asn Glu Asp Lys Ala Ala Ala Ile Leu Glu Ala Trp Gln
385                 390                 395                 400

Arg Thr Tyr Val Glu Val Val His Gln Ser Val Ala Gln Asn Ser Thr
                405                 410                 415

Gln Lys Val Leu Ser Phe Thr Thr Thr Leu Asp Asp Ile Leu Lys
        420                 425                 430

Ser Phe Ser Asp Val Ser Val Ile Arg Val Ala Ser Gly Tyr Leu Leu
    435                 440                 445

Met Leu Ala Tyr Ala Cys Leu Thr Met Leu Arg Trp Asp Cys Ser Lys
450                 455                 460

Ser Gln Gly Ala Val Gly Leu Ala Gly Val Leu Leu Val Ala Leu Ser
465                 470                 475                 480

Val Ala Ala Gly Leu Gly Leu Cys Ser Leu Ile Gly Ile Ser Phe Asn
                485                 490                 495

Ala Ala Thr Thr Gln Val Leu Pro Phe Leu Ala Leu Gly Val Gly Val
            500                 505                 510

Asp Asp Val Phe Leu Leu Ala His Ala Phe Ser Glu Thr Gly Gln Asn
        515                 520                 525

Lys Arg Ile Pro Phe Glu Asp Arg Thr Gly Glu Cys Leu Lys Arg Thr
    530                 535                 540

Gly Ala Ser Val Ala Leu Thr Ser Ile Ser Asn Val Thr Ala Phe Phe
545                 550                 555                 560
```

-continued

```
Met Ala Ala Leu Ile Pro Ile Pro Ala Leu Arg Ala Phe Ser Leu Gln
            565                 570                 575

Ala Ala Val Val Val Val Phe Asn Phe Ala Met Val Leu Leu Ile Phe
            580                 585                 590

Pro Ala Ile Leu Ser Met Asp Leu Tyr Arg Arg Glu Asp Arg Arg Leu
            595                 600                 605

Asp Ile Phe Cys Cys Phe Thr Ser Pro Cys Val Ser Arg Val Ile Gln
610                 615                 620

Val Glu Pro Gln Ala Tyr Thr Asp Thr His Asp Asn Thr Arg Tyr Ser
625                 630                 635                 640

Pro Pro Pro Pro Tyr Ser Ser His Ser Phe Ala His Glu Thr Gln Ile
                    645                 650                 655

Thr Met Gln Ser Thr Val Gln Leu Arg Thr Glu Tyr Asp Pro His Thr
            660                 665                 670

His Val Tyr Tyr Thr Thr Ala Glu Pro Arg Ser Glu Ile Ser Val Gln
            675                 680                 685

Pro Val Thr Val Thr Gln Asp Thr Leu Ser Cys Gln Ser Pro Glu Ser
            690                 695                 700

Thr Ser Ser Thr Arg Asp Leu Leu Ser Gln Phe Ser Asp Ser Ser Leu
705                 710                 715                 720

His Cys Leu Glu Pro Pro Cys Thr Lys Trp Thr Leu Ser Ser Phe Ala
                    725                 730                 735

Glu Lys His Tyr Ala Pro Phe Leu Leu Lys Pro Lys Ala Lys Val Val
            740                 745                 750

Val Ile Phe Leu Phe Leu Gly Leu Leu Gly Val Ser Leu Tyr Gly Thr
            755                 760                 765

Thr Arg Val Arg Asp Gly Leu Asp Leu Thr Asp Ile Val Pro Arg Glu
            770                 775                 780

Thr Arg Glu Tyr Asp Phe Ile Ala Ala Gln Phe Lys Tyr Phe Ser Phe
785                 790                 795                 800

Tyr Asn Met Tyr Ile Val Thr Gln Lys Ala Asp Tyr Pro Asn Ile Gln
                    805                 810                 815

His Leu Leu Tyr Asp Leu His Arg Ser Phe Ser Asn Val Lys Tyr Val
                    820                 825                 830

Met Leu Glu Glu Asn Lys Gln Leu Pro Lys Met Trp Leu His Tyr Phe
            835                 840                 845

Arg Asp Trp Leu Gln Gly Leu Gln Asp Ala Phe Asp Ser Asp Trp Glu
            850                 855                 860

Thr Gly Lys Ile Met Pro Asn Asn Tyr Lys Asn Gly Ser Asp Asp Gly
865                 870                 875                 880

Val Leu Ala Tyr Lys Leu Leu Val Gln Thr Gly Ser Arg Asp Lys Pro
                    885                 890                 895

Ile Asp Ile Ser Gln Leu Thr Lys Gln Arg Leu Val Asp Ala Asp Gly
                    900                 905                 910

Ile Ile Asn Pro Ser Ala Phe Tyr Ile Tyr Leu Thr Ala Trp Val Ser
            915                 920                 925

Asn Asp Pro Val Ala Tyr Ala Ala Ser Gln Ala Asn Ile Arg Pro His
            930                 935                 940

Arg Pro Glu Trp Val His Asp Lys Ala Asp Tyr Met Pro Glu Thr Arg
945                 950                 955                 960

Leu Arg Ile Pro Ala Ala Glu Pro Ile Glu Tyr Ala Gln Phe Pro Phe
                    965                 970                 975

Tyr Leu Asn Gly Leu Arg Asp Thr Ser Asp Phe Val Glu Ala Ile Glu
```

-continued

```
                  980                 985                 990
Lys Val Arg Thr Ile Cys Ser Asn Tyr Thr Ser Leu Gly Leu Ser Ser
                995                1000               1005
Tyr Pro Asn Gly Tyr Pro Phe Leu Phe Trp Glu Gln Tyr Ile Gly Leu
           1010                1015                1020
Arg His Trp Leu Leu Leu Phe Ile Ser Val Val Leu Ala Cys Thr Phe
1025               1030                1035                1040
Leu Val Cys Ala Val Phe Leu Leu Asn Pro Trp Thr Ala Gly Ile Ile
           1045                1050                1055
Val Met Val Leu Ala Leu Met Thr Val Glu Leu Phe Gly Met Met Gly
           1060                1065                1070
Leu Ile Gly Ile Lys Leu Ser Ala Val Pro Val Ile Leu Ile Ala
           1075                1080                1085
Ser Val Gly Ile Gly Val Glu Phe Thr Val His Val Ala Leu Ala Phe
           1090                1095                1100
Leu Thr Ala Ile Gly Asp Lys Asn Arg Arg Ala Val Leu Ala Leu Glu
1105               1110                1115                1120
His Met Phe Ala Pro Val Leu Asp Gly Ala Val Ser Thr Leu Leu Gly
               1125                1130                1135
Val Leu Met Leu Ala Gly Ser Glu Phe Asp Phe Ile Val Arg Tyr Phe
               1140                1145                1150
Phe Ala Val Leu Ala Ile Leu Thr Ile Leu Gly Val Leu Asn Gly Leu
               1155                1160                1165
Val Leu Leu Pro Val Leu Leu Ser Phe Phe Gly Pro Tyr Pro Glu Val
           1170                1175                1180
Ser Pro Ala Asn Gly Leu Asn Arg Leu Pro Thr Pro Ser Pro Glu Pro
1185               1190                1195                1200
Pro Pro Ser Val Val Arg Phe Ala Met Pro Pro Gly His Thr His Ser
               1205                1210                1215
Gly Ser Asp Ser Ser Asp Ser Glu Tyr Ser Ser Gln Thr Thr Val Ser
               1220                1225                1230
Gly Leu Ser Glu Glu Leu Arg His Tyr Glu Ala Gln Gln Gly Ala Gly
           1235                1240                1245
Gly Pro Ala His Gln Val Ile Val Glu Ala Thr Glu Asn Pro Val Phe
           1250                1255                1260
Ala His Ser Thr Val Val His Pro Glu Ser Arg His His Pro Pro Ser
1265               1270                1275                1280
Asn Pro Arg Gln Gln Pro His Leu Asp Ser Gly Ser Leu Pro Pro Gly
               1285                1290                1295
Arg Gln Gly Gln Gln Pro Arg Arg Asp Pro Arg Glu Gly Leu Trp
           1300                1305                1310
Pro Pro Leu Tyr Arg Pro Arg Arg Asp Ala Phe Glu Ile Ser Thr Glu
           1315                1320                1325
Gly His Ser Gly Pro Ser Asn Arg Ala Arg Trp Gly Pro Arg Gly Ala
           1330                1335                1340
Arg Ser His Asn Pro Arg Asn Pro Ala Ser Thr Ala Met Gly Ser Ser
1345               1350                1355                1360
Val Pro Gly Tyr Cys Gln Pro Ile Thr Thr Val Thr Ala Ser Ala Ser
               1365                1370                1375
Val Thr Val Ala Val His Pro Pro Val Pro Gly Pro Gly Arg Asn
           1380                1385                1390
Pro Arg Gly Gly Leu Cys Pro Gly Tyr Pro Glu Thr Asp His Gly Leu
           1395                1400                1405
```

```
Phe Glu Asp Pro His Val Pro Phe His Val Arg Cys Glu Arg Arg Asp
    1410                1415                1420

Ser Lys Val Glu Val Ile Glu Leu Gln Asp Val Glu Cys Glu Glu Arg
1425                1430                1435                1440

Pro Arg Gly Ser Ser Ser Asn
                1445
```

PATCHED GENES AND THEIR USE FOR DIAGNOSTICS

CROSS-REFERENCE TO RELATED APPLICATIONS

This application is a continuation-in-part of application Ser. No. 08/540,406, filed Jan. 6, 1995, now U.S. Pat. No. 5,837,538, which is a continuation-in-part of application Ser. No. 08/319,745, filed Oct. 7, 1994, now abandoned, the disclosures of which are herein incorporated by reference.

This invention was made with support from the Howard Hughes Medical Institute. The Government may have certain rights in this invention.

INTRODUCTION

1. Technical Field

The field of this invention is segment polarity genes and their uses.

2. Background

Segment polarity genes were originally discovered as mutations in flies that change the pattern of body segment structures. Mutations in these genes cause animals to develop changed patterns on the surfaces of body segments; the changes affecting the pattern along the head to tail axis. Among the genes in this class are hedgehog, which encodes a secreted protein (HH), and patched, which encodes a protein structurally similar to transporter proteins, having twelve transmembrane domains (PTC), with two conserved glycosylation signals.

The hedgehog gene of flies has at least three vertebrate relatives: Sonic hedgehog (Shh); Indian hedgehog (Ihh), and Desert hedgehog (Dhh). Shh is expressed in a group of cells, at the posterior of each developing limb bud, that have an important role in signaling polarity to the developing limb. The Shh protein product, SHH is a critical trigger of posterior limb development, and is also involved in polarizing the neural tube and somites along the dorsal ventral axis. Based on genetic experiments in flies, patched and hedgehog have antagonistic effects in development. The patched gene product, PTC, is widely expressed in fetal and adult tissues, and plays an important role in regulation of development. PTC downregulates transcription of itself, members of the transforming growth factor β and Wnt gene families, and possibly other genes. Among other activities, HH upregulates expression of patched and other genes that are negatively regulated by patched.

It is of interest that many genes involved in the regulation of growth and control of cellular signaling are also involved in oncogenesis. Such genes may be oncogenes, which are typically upregulated in tumor cells, or tumor suppressor genes, which are down-regulated or absent in tumor cells. Malignancies may arise when a tumor suppressor is lost and/or an oncogene is inappropriately activated. Familial predisposition to cancer may occur when there is a mutation, such as loss of an allele encoding a suppressor gene, present in the germlne DNA of an individual.

The most common form of cancer in the United States is basal cell carcinoma of the skin. While sporadic cases are very common, there are also familial syndromes, such as the basal cell nevus syndrome (BCNS). The familial syndrome has many features indicative of abnormal embryonic development, indicating that the mutated gene also plays an important role in development of the embryo. A loss of heterozygosity of chromosome 9q alleles in both familial and sporadic carcinomas suggests that a tumor suppressor gene is present in this region. The high incidence of skin cancer makes the identification of this putative tumor suppressor gene of great interest for diagnosis, therapy, and drug screening.

Relevant Literature

Descriptions of patched, by itself or its role with hedgehog may be found in Hooper and Scott (1989) *Cell* 59:751–765; and Nakano et al. (1989) *Nature* 341:508–513. Both of these references also describe the sequence for Drosophila patched. Discussions of the role of hedgehog include Riddle et al. (1993) *Cell* 75:1401–1416; Echelard et al. (1993) *Cell* 75:1417–1430; Krauss et al. (1993) *Cell* 75:1431–1444 (1993); Tabata and Kornberg (1994) *Cell* 76:89–102; Heemskerk and DiNardo (1994) *Cell* 76:449–460; and Roelink et al. (1994) *Cell* 76:761–775.

Mapping of deleted regions on chromosome 9 in skin cancers is described in Habuchi et al. (1995) *Oncogene* 11:1671–1674; Quinn et al. (1994) *Genes Chromosome Cancer* 11:222–225; Quinn et al. (1994) *J. Invest. Dermatol.* 102:300–303; and Wicking et al. (1994) *Genomics* 22:505–511.

Gorlin (1987) *Medicine* 66:98–113 reviews nevoid basal cell carcinoma syndrome. The syndrome shows autosomal dominant inheritance with probably complete penetrance. About 60% of the cases represent new mutations. Developmental abnormalities found with this syndrome include rib and craniofacial abnormalities, polydactyly, syndactyly and spina bifida. Tumors found with the syndrome include basal cell carcinomas, fibromas of the ovaries and heart, cysts of the skin, jaws and mesentery, meningiomas and medulloblastomas.

SUMMARY OF THE INVENTION

Isolated nucleotide compositions and sequences are provided for patched (ptc) genes, including mammalian, e.g. human and mouse, and invertebrate homologs. Decreased expression of ptc is associated with the occurrence of human cancers, particularly basal cell carcinomas of the skin. The cancers may be familial, having as a component of risk a germline mutation in the gene, or may be sporadic. ptc, and its antagonist hedgehog, are useful in creating transgenic animal models for these human cancers. The ptc nucleic acid compositions find use in identifying homologous or related genes; in producing compositions that modulate the expression or function of its encoded protein, PTC; for gene therapy; mapping functional regions of the protein; and in studying associated physiological pathways. In addition, modulation of the gene activity in vivo is used for prophylactic and therapeutic purposes, such as treatment of cancer, identification of cell type based on expression, and the like. PTC, anti-PTC antibodies and ptc nucleic acid sequences are useful as diagnostics for a genetic predisposition to cancer or developmental abnormality syndromes, and to identify specific cancers having mutations in this gene.

DATABASE REFERENCES FOR NUCLEOTIDE AND AMINO ACID SEQUENCES

Figure 1:
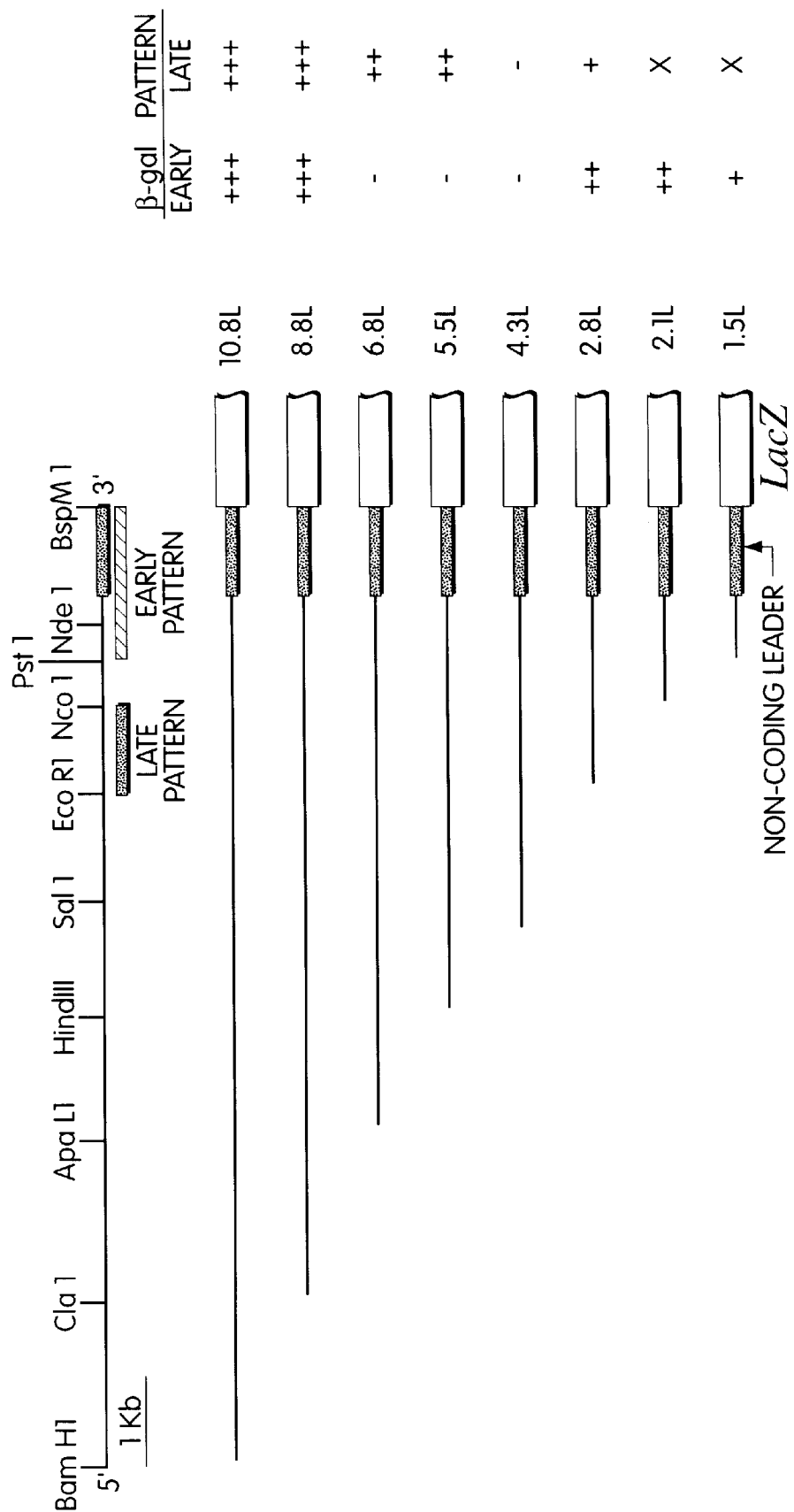
FIG. 1 is a graph having a restriction map of about 10 kbp of the 5' region upstream from the initiation codon of Drosophila patched gene and bar graphs of constructs of truncated portions of the 5' region joined to β-galactosidase, where the constructs are introduced into fly cell lines for the production of embryos. The expression of β-gal in the embryos is indicated in the right-hand table during early and late development of the embryo. The greater the number of +'s, the more intense the staining.

The sequence for the *D. melanogaster* patched gene has the Genbank accession number M28418. The sequence for the mouse patched gene has the Genbank accession number It30589-V46155. The sequence for the human patched gene has the Genbank accession number U59464.

DESCRIPTION OF THE SPECIFIC EMBODIMENTS

Mammalian and invertebrate patched (ptc) gene compositions and methods for their isolation are provided. Of particular interest are the human and mouse homologs. Certain human cancers, e.g. basal cell carcinoma, transitional cell carcinoma of the bladder, meningiomas, medulloblastomas, etc., show decreased ptc activity, resulting from oncogenic mutations at the ptc locus. Many such cancers are sporadic, where the tumor cells have a somatic mutation in ptc. The basal cell nevus syndrome (BCNS), an inherited disorder, is associated with germlne mutations in ptc. Such germlne mutations may also be associated with other human cancers. Decreased PTC activity is also associated with inherited developmental abnormalities, e.g. rib and craniofacial abnormalities, polydactyly, syndactyly and spina bifida.

The ptc genes and fragments thereof, encoded protein, and anti-PTC antibodies are useful in the identification of individuals predisposed to development of such cancers and developmental abnormalities, and in characterizing the phenotype of sporadic tumors that are associated with this gene. The characterization is useful for prenatal screening, and in determining further treatment of the patient. Tumors may be typed or staged as to the PTC status, e.g. by detection of mutated sequences, antibody detection of abnormal protein products, and functional assays for altered PTC activity. The encoded PTC protein is useful in drug screening for compositions that mimic PTC activity or expression, including altered forms of PTC protein, particularly with respect to PTC function as a tumor suppressor in oncogenesis.

The human and mouse ptc gene sequences and isolated nucleic acid compositions are provided. In identifying the mouse and human patched genes, cross-hybridization of DNA and amplification primers were employed to move through the evolutionary tree from the known Drosophila ptc sequence, identifying a number of invertebrate homologs. The human patched gene has been mapped to human chromosome band 9q22.3, and lies between the polymorphic markers D9S196 and D9S287 (a detailed map of human genome markers may be found in Dib et al. (1996) Nature 280:152; http://www.genethon.fr).

DNA from a patient having a tumor or developmental abnormality, which may be associated with ptc, is analyzed for the presence of a predisposing mutation in the ptc gene. The presence of a mutated ptc sequence that affects the activity or expression of the gene product, PTC, confers an increased susceptibility to one or more of these conditions. Individuals are screened by analyzing their DNA for the presence of a predisposing oncogenic or developmental mutation, as compared to a normal sequence. A "normal" sequence of patched is provided in SEQ ID NO:18 (human). Specific mutations of interest include any mutation that leads to oncogenesis or developmental abnormalities, including insertions, substitutions and deletions in the coding region sequence, introns that affect splicing, promoter or enhancer that affect the activity and expression of the protein.

Screening for tumors or developmental abnormalities may also be based on the functional or antigenic characteristics of the protein. Immunoassays designed to detect the normal or abnormal PTC protein may be used in screening. Where many diverse mutations lead to a particular disease phenotype, functional protein assays have proven to be effective screening tools. Such assays may be based on detecting changes in the transcriptional regulation mediated by PTC, or may directly detect PTC transporter activity, or may involve antibody localization of patched in cells.

Inheritance of BCNS is autosomal dominant, although many cases are the result of new mutations. Diagnosis of BCNS is performed by protein, DNA sequence or hybridization analysis of any convenient sample from a patient, e.g. biopsy material, blood sample, scrapings from cheek, etc. A typical patient genotype will have a predisposing mutation on one chromosome. In tumors and at least sometimes developmentally affected tissues, loss of heterozygosity at the ptc locus leads to aberrant cell and tissue behavior. When the normal copy of ptc is lost, leaving only the reduced function mutant copy, abnormal cell growth and reduced cell layer adhesion is the result. Examples of specific ptc mutations in BCNS patients are a 9 bp insertion at nt 2445 of the coding sequence; and an 11 bp deletion of nt 2441 to 2452 of the coding sequence. These result in insertions or deletions in the region of the seventh transmembrane domain.

Prenatal diagnosis of BCNS may be performed, particularly where there is a family history of the disease, e.g. an affected parent or sibling. It is desirable, although not required, in such cases to determine the specific predisposing mutation present in affected family members. A sample of fetal DNA, such as an amniocentesis sample, fetal nucleated or white blood cells isolated from maternal blood, chorionic villus sample, etc. is analyzed for the presence of the predisposing mutation. Alternatively, a protein based assay, e.g. functional assay or immunoassay, is performed on fetal cells known to express ptc.

Sporadic tumors associated with loss of PTC function include a number of carcinomas known to have deletions in the region of chromosome 9q22, e.g. basal cell carcinomas, transitional bladder cell carcinoma, meningiomas, medullomas, fibromas of the heart and ovary, and carcinomas of the lung, ovary, kidney and esophagus. Characterization of sporadic tumors will generally require analysis of tumor cell DNA, conveniently with a biopsy sample. A wide range of mutations are found in sporadic cases, up to and including deletion of the entire long arm of chromosome 9. Oncogenic mutations may delete one or more exons, e.g. 8 and 9, may affect the amino acid sequence of the extracellular loops or transmembrane domains, may cause truncation of the protein by introducing a frameshift or stop codon, etc. Specific examples of oncogenic mutations include a C to T transition at nt 523; and deletions encompassing exon 9. C to T transitions are characteristic of ultraviolet mutagenesis, as expected with cases of skin cancer.

Biochemical studies may be performed to determine whether a candidate sequence variation in the ptc coding region or control regions is oncogenic. For example, a change in the promoter or enhancer sequence that down-regulates expression of patched may result in predisposition to cancer. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, chloramphenical acetyltransferase, etc. that provides for convenient quantitation; and the like. The activity of the encoded PTC protein may be determined by comparison with the wild-type protein, e.g. by detection of transcriptional down-regulation of TGFβ, Wnt family genes, ptc itself, or reporter gene fusions involving these target genes.

The human patched gene (SEQ ID NO:18) has a 4.5 kb open reading frame encoding a protein of 1447 amino acids. Including coding and non-coding sequences, it is about 89% identical at the nucleotide level to the mouse patched gene (SEQ ID NO:09). The mouse patched gene (SEQ ID NO:09) encodes a protein (SEQ ID NO:10) that has about 38% identical amino acids to Drosophila PTC (SEQ ID NO:6), over about 1,200 amino acids. The butterfly homolog (SEQ ID NO:4) is 1,300 amino acids long and overall has a 50% amino acid identity to fly PTC (SEQ ID NO:6). A 267 bp exon from the beetle patched gene encodes an 89 amino acid protein fragment, which was found to be 44% and 51% identical to the corresponding regions of fly and butterfly PTC respectively.

The DNA sequence encoding PTC may be cDNA or genomic DNA or a fragment thereof. The term "patched gene" shall be intended to mean the open reading frame encoding specific PTC polypeptides, as well as adjacent 5' and 3' non-coding nucleotide sequences involved in the regulation of expression, up to about 1 kb beyond the coding region, in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons, 3' and 5' non-coding regions. Normally mRNA species have contiguous exons, with the intervening introns deleted, to create a continuous open reading frame encoding PTC.

The genomic ptc sequence has non-contiguous open reading frames, where introns interrupt the coding regions. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb of flanking genomic DNA at either the 5' or 3' end of the coding region. The genomic DNA may be isolated as a fragment of 50 kbp or smaller; and substantially free of flanking chromosomal sequence.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The ptc genes are isolated and obtained in substantial purity, generally as other than an intact mammalian chromosome. Usually, the DNA will be obtained substantially free of other nucleic acid sequences that do not include a ptc sequence or fragment thereof, generally being at least about 50%, usually at least about 90% pure and are typically "recombinant", ie. flanked by one or more nucleotides with which it is not normally associated on a naturally occurring chromosome.

The DNA sequences are used in a variety of ways. They may be used as probes for identifying other patched genes. Mammalian homologs have substantial sequence similarity to the subject sequences, i.e. at least 75%, usually at least 90%, more usually at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithims for sequence analysis are known in the art, such as BLAST, described in Altschul et aL. (1990) *J. Mol. Biol.* 215:403–10.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. By using probes, particularly labeled probes of DNA sequences, one can isolate homologous or related genes. The source of homologous genes may be any mammalian species, e.g. primate species, particularly human; murines, such as rats and mice, canines, felines, bovines, ovines, equines, etc.

The DNA may also be used to identify expression of the gene in a biological specimen. The manner in which one probes cells for the presence of particular nucleotide sequences, as genomic DNA or RNA, is well-established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose and then probed with a fragment of the subject DNA as a probe. Other techniques may also find use. Detection of mRNA having the subject sequence is indicative of patched gene expression in the sample.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; as an antisense sequence; or the like. Modifications may include replacing oxygen of the phosphate esters with sulfur or nitrogen, replacing the phosphate with phosphoramide, etc.

A number of methods are available for analyzing genomic DNA sequences. Where large amounts of DNA are available, the genomic DNA is used directly. Alternatively, the region of interest is cloned into a suitable vector and grown in sufficient quantity for analysis, or amplified by conventional techniques, such as the polymerase chain reaction (PCR). The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp. 14.2–14.33.

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to the normal ptc sequence. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilised on a solid support, as described in WO 95/11995, may also be used as a means of detecting the presence of variant sequences. Alternatively, where a predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels.

The subject nucleic acids can be used to generate transgenic animals or site specific gene modifications in cell lines. Transgenic animals may be made through homologous recombination, where the normal patched locus is altered. Alternatively, a nucleic acid construct is randomly integrated into the genome. Vectors for stable integration include plasmids, retroviruses and other animal viruses, YACs, and the like.

The modified cells or animals are useful in the study of patched function and regulation. For example, a series of small deletions and/or substitutions may be made in the patched gene to determine the role of different exons in oncogenesis, signal transduction, etc. Of particular interest are transgenic animal models for carcinomas of the skin, where expression of PTC is specifically reduced or absent in skin cells. An alternative approach to transgenic models for this disease are those where one of the mammalian hedgehog genes, e.g. Shh, Ihh, Dhh, are upregulated in skin cells, or in other cell types. For models of skin abnormalities, one may use a skin-specific promoter to drive expression of the transgene, or other inducible promoter that can be regulated in the animal model. Such promoters include keratin gene promoters. Specific constructs of interest include anti-sense ptc, which will block PTC expression, expression of dominant negative PTC mutations, and over-expression of HH genes. A detectable marker, such as lac Z may be introduced into the patched locus, where upregulation of patched expression will result in an easily detected change in phenotype.

One may also provide for expression of the patched gene or variants thereof in cells or tissues where it is not normally expressed or at abnormal times of development. Thus, mouse models of spina bifida or abnormal motor neuron differentiation in the developing spinal cord are made available. In addition, by providing expression of PTC protein in cells in which it is otherwise not normally produced, one can induce changes in cell behavior, e.g. through PTC mediated transcription modulation.

DNA constructs for homologous recombination will comprise at least a portion of the patched or hedgehog gene with the desired genetic modification, and will include regions of homology to the target locus. DNA constructs for for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or ES cells may be obtained freshly from a host, e.g. mouse, rat, guinea pig, etc. Such cells are grown on an appropriate fibroblast-feeder layer or grown in the presence of leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on basal cell carcinomas.

The subject gene may be employed for producing all or portions of the patched protein. For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host.

Figure 2:
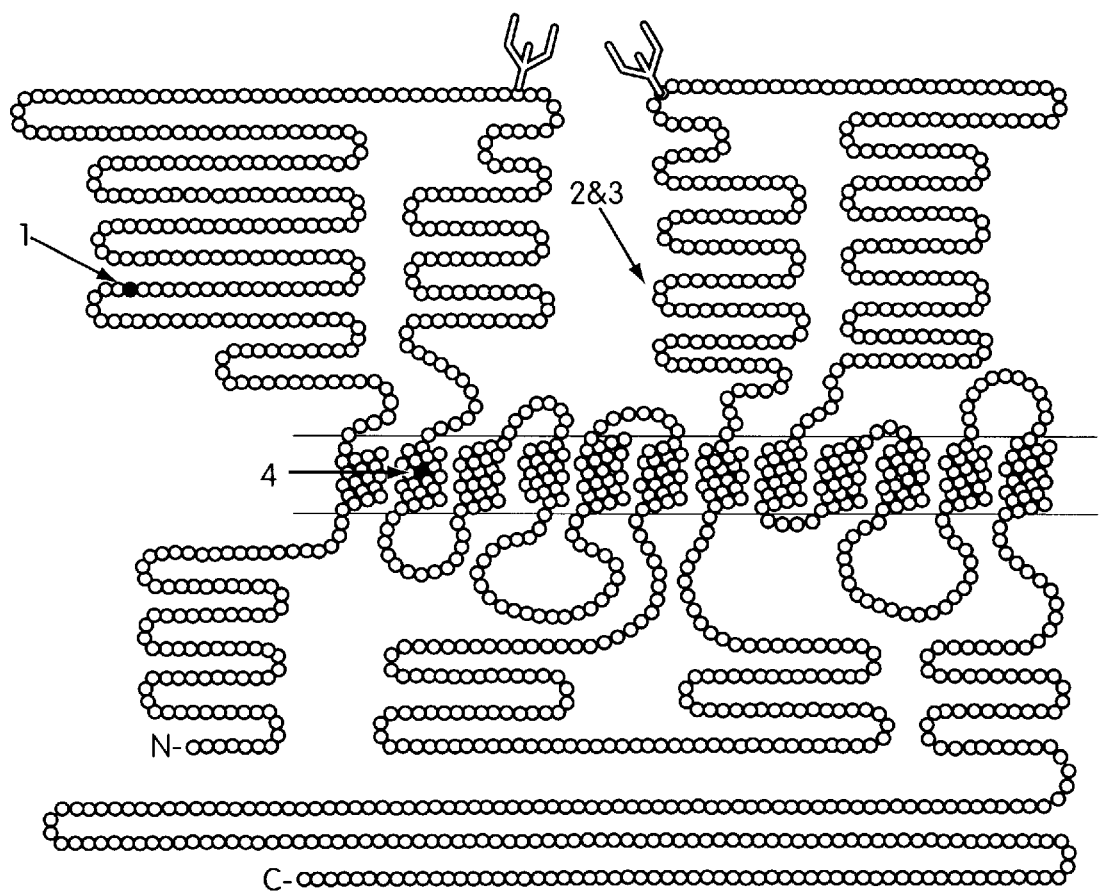
FIG. 2 shows a summary of mutations found in the human patched gene locus that are associated with basal cell nevus syndrome. Mutation (1) is found in sporadic basal cell carcinoma, and is a C to T transition in exon 3 at nucleotide 523 of the coding sequence, changing Leu 175 to Phe in the first extracellular loop. Mutations 2–4 are found in hereditary basal carcinoma nevus syndrome. (2) is an insertion of 9 bp at nucleotide 2445, resulting in the insertion of an additional 3 amino acids after amino acid 815. (3) is a deletion of 11 bp, which removes nt 2442–2452 from the coding sequence. The resulting frameshift truncates the open reading frame after amino acid 813, just after the seventh transmembrane domain. (4) is a G to C alteration that changes two conserved nucleotides of the 3' splice site adjacent to exon 10, creating a non-functional splice site that truncates the protein after amino acid 449, in the second transmembrane region.

Specific PTC peptides of interest include the extracellular domains, particularly in the human mature protein, aa 120 to 437, and aa 770 to 1027. These peptides may be used as immunogens to raise antibodies that recognize the protein in an intact cell membrane. The cytoplasmic domains, as shown in FIG. 2, (the amino terminus and carboxy terminus) are of interest in binding assays to detect ligands involved in signaling mediated by PTC.

The peptide may be expressed in prokaryotes or eukaryotes in accordance with conventional ways, depending upon the purpose for expression. For large scale production of the protein, a unicellular organism or cells of a higher organism, e.g. eukaryotes such as vertebrates, particularly mammals, may be used as the expression host, such as *E. coli, B, subtilis, S. cerevisiae*, and the like. In many situations, it may be desirable to express the patched gene in a mammalian host, whereby the patched gene will be glycosylated, and transported to the cellular membrane for various studies.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. By pure is intended free of other proteins, as well as cellular debris.

The polypeptide is used for the production of antibodies, where short fragments provide for antibodies specific for the particular polypeptide, whereas larger fragments or the entire gene allow for the production of antibodies over the surface of the polypeptide or protein. Antibodies may be raised to the normal or mutated forms of PTC. The extracellular domains of the protein are of interest as epitopes, particular antibodies that recognize common changes found in abnormal, oncogenic PTC, which compromise the protein activity. Antibodies may be raised to isolated peptides corresponding to these domains, or to the native protein, e.g. by immunization with cells expressing PTC, immunization with liposomes having PTC inserted in the membrane, etc. Antibodies that recognize the extracellular domains of PTC are useful in diagnosis, typing and staging of human carcinomas.

Antibodies are prepared in accordance with conventional ways, where the expressed polypeptide or protein may be used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen may be isolated, the splenocytes immortalized, and then screened for high affinity antibody binding. The immortalized cells, e.g. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutigenized by cloning in *E. coli*, and the heavy and light chains may be mixed to further enhance the affinity of the antibody.

The antibodies find particular use in diagnostic assays for developmental abnormalities, basal cell carcinomas and other tumors associated with mutations in PTC. Staging, detection and typing of tumors may utilize a quantitative immunoassay for the presence or absence of normal PTC. Alternatively, the presence of mutated forms of PTC may be determined. A reduction in normal PTC and/or presence of abnormal PTC is indicative that the tumor is PTC-associated.

A sample is taken from a patient suspected of having a PTC-associated tumor, developmental abnormality or BCNS. Samples, as used herein, include biological fluids such as blood, cerebrospinal fluid, tears, saliva, lymph, dialysis fluid and the like; organ or tissue culture derived fluids; and fluids extracted from physiological tissues. Also included in the term are derivatives and fractions of such fluids. Biopsy samples are of particular interest, e.g. skin lesions, organ tissue fragments, etc. Where metastasis is suspected, blood samples may be preferred. The number of cells in a sample will generally be at least about $10^3$, usually at least $10^4$ more usually at least about $10^5$. The cells may be dissociated, in the case of solid tissues, or tissue sections may be analyzed. Alternatatively a lysate of the cells may be prepared.

Diagnosis may be performed by a number of methods. The different methods all determine the absence or presence of normal or abnormal PTC in patient cells suspected of having a mutation in PTC. For example, detection may utilize staining of intact cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well-known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and PTC in a lysate. Measuring the concentration of PTC binding in a sample or fraction thereof may be accomplished by a variety of specific assays. A conventional sandwich type assay may be used. For example, a sandwich assay may first attach PTC-specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of normal and/or abnormal PTC is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind PTC with sufficient specificity such that it can be distinguished from other components present. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for PTC as desired, conveniently using a labeling method as described for the sandwich assay.

Other diagnostic assays of interest are based on the functional properties of PTC protein itself. Such assays are particularly useful where a large number of different sequence changes lead to a common phenotype, i.e. loss of protein function leading to oncogenesis or developmental abnormality. For example, a functional assay may be based on the transcriptional changes mediated by hedgehog and patched gene products. Addition of soluble Hh to embryonic stem cells causes induction of transcription in target genes. The presence of functional PTC can be determined by its ability to antagonize Hh activity. Other functional assays may detect the transport of specific molecules mediated by PTC, in an intact cell or membrane fragment. Conveniently, a labeled substrate is used, where the transport in or out of the cell can be quantitated by radiography, microscopy, flow cytometry, spectrophotometry, etc. Other assays may detect conformational changes, or changes in the subcellular localization of patched protein.

By providing for the production of large amounts of patched protein, one can identify ligands or substrates that bind to, modulate or mimic the action of patched. A common feature in basal cell carcinoma is the loss of adhesion between epidermal and dermal layers, indicating a role for PTC in maintaining appropriate cell adhesion. Areas of investigation include the development of cancer treatments, wound healing, adverse effects of aging, metastasis, etc.

Drug screening identifies agents that provide a replacement for PTC function in abnormal cells. The role of PTC as a tumor suppressor indicates that agents which mimic its function, in terms of transmembrane transport of molecules, transcriptional down-regulation, etc., will inhibit the process of oncogenesis. These agents may also promote appropriate cell adhesion in wound healing and aging, to reverse the loss of adhesion observed in metastasis, etc. Conversely, agents that reverse PTC function may stimulate controlled growth and healing. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, transporter function, etc.

The term "agent" as used herein describes any molecule, e.g. protein or pharmaceutical, with the capability of altering or mimicking the physiological function of patched. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic patched function, such as repression of target gene transcription, transport of patched substrate compounds, etc. For example, an expression construct comprising a patched gene may be introduced into a cell line under conditions that allow expression. The level of patched activity is determined by a functional assay, as previously described. In one screening assay, candidate agents are added in combination with a Hh protein, and the ability to overcome Hh antagonism of PTC is detected. In another assay, the ability of candidate agents to enhance PTC function is determined. Alternatively, candidate agents are added to a cell that lacks functional PTC, and screened for the ability to reproduce PTC in a functional assay.

The compounds having the desired pharmacological activity may be administered in a physiologically acceptable carrier to a host for treatment of cancer or developmental abnormalities attributable to a defect in patched function. The compounds may also be used to enhance patched function in wound healing, aging, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The gene or fragments thereof may be used as probes for identifying the 5' non-coding region comprising the transcriptional initiation region, particularly the enhancer regulating the transcription of patched. By probing a genomic library, particularly with a probe comprising the 5' coding region, one can obtain fragments comprising the 5' non-coding region. If necessary, one may walk the fragment to obtain further 5' sequence to ensure that one has at least a functional portion of the enhancer. It is found that the enhancer is proximal to the 5' coding region, a portion being in the transcribed sequence and downstream from the promoter sequences. The transcriptional initiation region may be used for many purposes, studying embryonic development, providing for regulated expression of patched protein or other protein of interest during embryonic development or thereafter, and in gene therapy.

The gene may also be used for gene therapy. Vectors useful for introduction of the gene include plasmids and viral vectors. Of particular interest are retroviral-based vectors, e.g. moloney murine leukemia virus and modified human immunodeficiency virus; adenovirus vectors, etc. Gene therapy may be used to treat skin lesions, an affected fetus, etc., by transfection of the normal gene into embryonic stem cells or into other fetal cells. A wide variety of viral vectors can be employed for transfection and stable integration of the gene into the genome of the cells. Alternatively, micro-injection may be employed, fusion, or the like for introduction of genes into a suitable host cell. See, for example, Dhawan et al. (1991) *Science* 254:1509–1512 and Smith et al. (1990) *Molecular and Cellular Biology* 3268–3271.

The following examples are offered by illustration not by way of limitation.

EXPERIMENTAL

Methods and Materials

PCR on Mosquito (*Anopheles gambiae*) Genomic DNA. PCR primers were based on amino acid stretches of fly PTC that were not likely to diverge over evolutionary time and were of low degeneracy. Two such primers (P2R1 (SEQ ID NO:14): GGACGTTCAARGTNCAYCARYTNTGG, P4R1: (SEQ ID NO:15) GGACGMTTCCYTCCCARAARCANTC, (the underlined sequences are Eco RI linkers) amplified an appropriately sized band from mosquito genomic DNA using the PCR. The program conditions were as follows:

94° C. 4 min.; 72° C. Add Taq;

[49° C. 30 sec.; 72° C. 90 sec.; 94° C. 15 sec] 3 times

[94° C. 15 sec.; 50° C. 30 sec.; 72° C. 90 sec] 35 times

72° C. 10 min; 4° C. hold

This band was subcloned into the EcoRV site of pBluescript II and sequenced using the USB Sequence kit.

Screen of a Butterfly cDNA Library with Mosquito PCR Product. Using the mosquito PCR product (SEQ ID NO:7) as a probe, a 3 day embryonic *Precis coenia* λgt10 cDNA library (generously provided by Sean Carroll) was screened. Filters were hybridized at 65° C. overnight in a solution containing 5×SSC, 10% dextran sulfate, 5× Denhardt's, 200 μg/ml sonicated salmon sperm DNA, and 0.5% SDS. Filters were washed in 0.1×SSC, 0.1% SDS at room temperature several times to remove nonspecific hybridization. Of the 100,000 plaques initially screened, 2 overlapping clones, L1 and L2, were isolated, which corresponded to the N terminus of butterfly PTC. Using L2 as a probe, the library filters were rescreened and 3 additional clones (L5, L7, L8) were isolated which encompassed the remainder of the ptc coding sequence. The full length sequence of butterfly ptc (SEQ ID NO:3) was determined by ABI automated sequencing.

Screen of a Tribolium (beetle) Genomic Library with Mosquito PCR Product and 900 bp Fragment from the Butterfly Clone. A λgem11 genomic library from *Tribolium casteneum* (gift of Rob Dennell) was probed with a mixture of the mosquito PCR (SEQ ID NO:7) product and BstXI/EcoRI fragment of L2. Filters were hybridized at 55° C. overnight and washed as above. Of the 75,000 plaques screened, 14 clones were identified and the SacI fragment of T8 (SEQ ID NO:1), which crosshybridized with the mosquito and butterfly probes, was subcloned into pBluescript.

PCR on Mouse cDNA Using Degenerate Primers Derived from Regions Conserved in the Four Insect Homologues. Two degenerate PCR primers (P4REV: (SEQ ID NO:16) GGACGAATTCYTNGANTGYTTYTGGGA; P22: (SEQ ID NO:17) CATACCAGCCAAGCTTGTCIGGCCARTGCAT) were designed based on a comparison of PTC amino acid sequences from fly (*Drosophila melanogaster*) (SEQ ID NO:6), mosquito (*Anopheles gambiae*)(SEQ ID NO:8), butterfly (*Precis coenia*)(SEQ ID NO:4), and beetle (*Tribolium casteneum*)(SEQ ID NO:2). I represents inosine, which can form base pairs with all four nucleotides. P22 was used to reverse transcribe RNA from 12.5 dpc mouse limb bud (gift from David Kingsley) for 90 min at 37° C. PCR using P4REV(SEQ ID NO:17) and P22(SEQ ID NO:18) was then performed on 1 μl of the resultant cDNA under the following conditions:

94° C. 4 min.; 72° C. Add Taq;
[94° C. 15 sec.; 50° C. 30 sec.; 72° C. 90 sec.] 35 times
72° C. 10 min.; 4° C. hold PCR products of the expected size were subcloned into the TA vector (Invitrogen) and sequenced with the Sequenase Version 2.0 DNA Sequencing Kit (U.S.B.).

Using the cloned mouse PCR fragment as a probe, 300,000 plaques of a mouse 8.5 dpc λgt10 cDNA library (a gift from Brigid Hogan) were screened at 65° C. as above and washed in 2×SSC, 0.1% SDS at room temperature. 7 clones were isolated, and three (M2 M4, and M8) were subcloned into pBluescript II. 200,000 plaques of this library were rescreened using first, a 1.1 kb EcoRI fragment from M2 to identify 6 clones (M9–M16) and secondly a mixed probe containing the most N terminal (Xhol fragment from M2) and most C terminal sequences (BamHI/BglII fragment from M9) to isolate 5 clones (M17–M21). M9, M10, M14, and M17–21 were subcloned into the EcoRI site of pBluescript II (Strategene).

RNA Blots and in situ Hybridizations in Whole and Sectioned Mouse Embryos:

Northerns. A mouse embryonic Northern blot and an adult multiple tissue Northern blot (obtained from Clontech) were probed with a 900 bp EcoRI fragment from an N terminal coding region of mouse ptc. Hybridization was performed at 65° C. in 5×SSPE, 10× Denhardt's, 100 μg/ml sonicated salmon sperm DNA, and 2% SDS. After several short room temperature washes in 2× SSC, 0.05% SDS, the blots were washed at high stringency in 0.1×SSC, 0.1% SDS at 50 C.

In situ hybridization of sections: 7.75, 8.5, 11.5, and 13.5 dpc mouse embryos were dissected in PBS and frozen in Tissue-Tek medium at −80° C. 12–16 μm frozen sections were cut, collected onto VectaBond (Vector Laboratories) coated slides, and dried for 30–60 minutes at room temperature. After a 10 minute fixation in 4% paraformaldehyde in PBS, the slides were washed 3 times for 3 minutes in PBS, acetylated for 10 minutes in 0.25% acetic anhydride in triethanolamine, and washed three more times for 5 minutes in PBS. Prehybridization (50% formamide, 5×SSC, 250 μg/ml yeast tRNA, 500 μg/ml sonicated salmon sperm DNA, and 5× Denhardt's) was carried out for 6 hours at room temperature in 50% formamide/5×SSC humidified chambers. The probe, which consisted of 1 kb from the N-terminus of ptc, was added at a concentration of 200–1000 ng/ml into the same solution used for prehybridization, and then denatured for five minutes at 80° C. Approximately 75 μl of probe were added to each slide and covered with Parafilm. The slides were incubated overnight at 65° C. in the same humidified chamber used previously. The following day, the probe was washed successively in 5×SSC (5 minutes, 65° C.), 0.2×SSC (1 hour, 65° C.), and 0.2×SSC (10 minutes, room temperature). After five minutes in buffer B1 (0.1M maleic acid, 0.15 M NaCl, pH 7.5), the slides were blocked for 1 hour at room temperature in 1% blocking reagent (Boerhinger-Mannheim) in buffer B1, and then incubated for 4 hours in buffer B1 containing the DIG-AP conjugated antibody (Boerhinger-Mannheim) at a 1:5000 dilution. Excess antibody was removed during two 15 minute washes in buffer B1, followed by five minutes in buffer B3 (100 mM Tris, 100 mM NaCl, 5 mM MgCl$_2$, pH 9.5). The antibody was detected by adding an alkaline phosphatase substrate (350 μl 75 mg/ml X-phosphate in DMF, 450 μl 50 mg/ml NBT in 70% DMF in 100 mls of buffer B3) and allowing the reaction to proceed over-night in the dark. After a brief rinse in 10 mM Tris, 1 mM EDTA, pH 8.0, the slides were mounted with Aquamount (Lerner Laboratories).

Drosophila 5-transcriptional initiation region β-gal constructs. A series of constructs were designed that link different regions of the ptc promoter from Drosophila to a LacZ reporter gene in order to study the cis regulation of the ptc expression pattern. See FIG. 1. A 10.8 kb BamHI/BspM1 fragment comprising the 5'-non-coding region of the mRNA at its 3'-terminus was obtained and truncated by restriction enzyme digestion as shown in FIG. 1. These expression cassettes were introduced into Drosophila lines using a P-element vector (Thummel et al. (1988) *Gene* 74:445–456), which were injected into embryos, providing flies which could be grown to produce embryos. (See Spradling and Rubin (1982) *Science* 218:341–347 for a description of the procedure.) The vector used a pUC8 background into which was introduced the white gene to provide for yellow eyes, portions of the P-element for integration, and the constructs were inserted into a polylinker upstream from the LacZ gene. The resulting embryos, larvae, and adults were stained using antibodies to LacZ protein conjugated to HRP and the samples developed with OPD dye to identify the expression of the LacZ gene. The staining pattern in embryos is described in FIG. 1, indicating whether there was staining during the early and late development of the embryo.

Isolation of a Mouse ptc Gene. Homologues of fly PTC (SEQ ID NO:6) were isolated from three insects: mosquito, butterfly and beetle, using either PCR or low stringency library screens. PCR primers to six amino acid stretches of PTC of low mutatability and degeneracy were designed. One primer pair, P2 and P4, amplified an homologous fragment of ptc from mosquito genomic DNA that corresponded to the first hydrophilic loop of the protein. The 345 bp PCR product (SEQ ID NO:7) was subcloned and sequenced and when aligned to fly PTC, showed 67% amino acid identity.

The cloned mosquito fragment was used to screen a butterfly λgt 10 cDNA library. Of 100,000 plaques screened, five overlapping clones were isolated and used to obtain the full length coding sequence. The butterfly PTC homologue (SEQ ID NO:4) is 1,311 amino acids long and overall has 50% amino acid identity (72% similarity) to fly PTC. With the exception of a divergent C-terminus, this homology is evenly spread across the coding sequence. The mosquito PCR clone (SEQ ID NO:7) and a corresponding fragment of butterfly cDNA were used to screen a beetle λgem11 genomic library. Of the plaques screened, 14 clones were identified. A fragment of one clone (T8), which hybridized with the original probes, was subcloned and sequenced. This 3 kb piece contains an 89 amino acid exon (SEQ ID NO:2) which is 44% and 51% identical to the corresponding regions of fly and butterfly PTC respectively.

Using an alignment of the four insect homologues in the first hydrophilic loop of the PTC, two PCR primers were designed to a five and six amino acid stretch which were identical and of low degeneracy. These primers were used to isolate the mouse homologue using RT-PCR on embryonic limb bud RNA. An appropriately sized band was amplified and upon cloning and sequencing, it was found to encode a protein 65% identical to fly PTC. Using the cloned PCR product and subsequently, fragments of mouse ptc cDNA, a mouse embryonic λcDNA library was screened. From about 300,000 plaques, 17 clones were identified and of these, 7 form overlapping cDNA's that comprise most of the protein-coding sequence (SEQ ID NO:9).

Developmental and Tissue Distribution of Mouse PTC RNA. In both the embryonic and adult Northern blots, the ptc probe detects a single 8 kb message. Further exposure does not reveal any additional minor bands. Developmentally, ptc mRNA is present in low levels as early as 7 dpc and becomes quite abundant by 11 and 15 dpc. While the gene is still present at 17 dpc, the Northern blot indicates a clear decrease in the amount of message at this stage. In the adult, ptc RNA is present in high amounts in the brain and lung, as well as in moderate amounts in the kidney and liver. Weak signals are detected in heart, spleen, skeletal muscle, and testes.

In situ Hybridization of Mouse PTC in Whole and Section Embryos. Northern analysis indicates that ptc mRNA is present at 7 dpc, while there is no detectable signal in sections from 7.75 dpc embryos. This discrepancy is explained by the low level of transcription. In contrast, ptc is present at high levels along the neural axis of 8.5 dpc embryos. By 11.5 dpc, ptc can be detected in the developing lung buds and gut, consistent with its adult Northern profile. In addition, the gene is present at high levels in the ventricular zone of the central nervous system, as well as in the zona limitans of the prosencephalon. ptc is also strongly transcribed in the condensing cartilage of 11.5 and 13.5 dpc limb buds, as well as in the ventral portion of the somites, a region which is prospective sclerotome and eventually forms bone in the vertebral column. ptc is present in a wide range of tissues from endodermal, mesodermal and ectodermal origin supporting its fundamental role in embryonic development.

Isolation of the Human ptc Gene. To isolate human ptc (hptc), $2 \times 10^5$ plaques from a human lung cDNA library (HL3022a, Clonetech) were screened with a 1 kbp mouse ptc fragment, M2-2. Filters were hybridized overnight at reduced stringency (60° C. in 5×SSC, 10% dextran sulfate, 5× Denhardt's, 0.2 mg/ml sonicated salmon sperm DNA, and 0.5% SDS). Two positive plaques (H1 and H2) were isolated, the inserts cloned into pBluescript, and upon sequencing, both contained sequence highly similar to the mouse ptc homolog. To isolate the 5' end, an additional $6 \times 10^5$ plaques were screened in duplicate with M2-3 EcoR I and M2-3 Xho I (containing 5' untranslated sequence of mouse ptc) probes. Ten plaques were purified and of these, 6 inserts were subloned into pBluescript. To obtain the full coding sequence, H2 was fully and H14, H20, and H21 were partially sequenced. The 5.1 kbp of human ptc sequence (SEQ ID NO:18) contains an open reading frame of 1447 amino acids (SEQ ID NO:19) that is 96% identical and 98% similar to mouse ptc. The 5' and 3' untranslated sequences of human ptc (SEQ ID NO:18) are also highly similar to mouse ptc (SEQ ID NO:09) suggesting conserved regulatory sequence.

Comparison of Mouse, Human, Fly and Butterfly Sequences. The deduced mouse PTC protein sequence (SEQ ID NO:10) has about 38% identical amino acids to fly PTC over about 1,200 amino acids. This amount of conservation is dispersed through much of the protein excepting the C-terminal region. The mouse protein also has a 50 amino acid insert relative to the fly protein. Based on the sequence conservation of PTC and the functional conservation of hedgehog between fly and mouse, one concludes that ptc functions similarly in the two organisms. A comparison of the amino acid sequences of mouse (mptc) (SEQ ID NO:10), human (hptc) (SEQ ID NO:19), butterfly (bptc)(SEQ ID NO:4) and drosophila (ptc) (SEQ ID NO.6) is shown in Table 1.

TABLE 1 alignment of human, mouse, fly, and butterfly PTC homologs

```
HPTC   MASAGNAAEPQDR--GGGGSGCIGAPGRPAGGGRRRRTGGLRRAAAPDRDYLHRPSYCDA
MPTC   MASAGNAA--------------GALGRQAGGGRRRRTGGPHRA-APDRDYLHRPSYCDA
PTC    M-----DRDSLPRVPDTHGD--VVDE---------KLFSDL---------YI-RTSWVDA
BPTC   MVAPDSEAPSNPRITAAHESPCATEA---------RHSADL---------YI-RTSWVDA
       *                            . ..            *. * * **

HPTC   AFALEQISKGKATGRKAPLWLRAKFQRLLFKLGCYIQKNCGKFLVVGLLIFGAFAVGLKA
MPTC   AFALEQISKGKATGRKAPLWLRAKFQRLLFKLGCYIQKNCGKFLVVGLLIFGAFAVGLKA
PTC    QVALDQIDKGKARGSRTAIYLRSVFQSHLETLGSSVQKHAGKVLFVAILVLSTFCVGLKS
BPTC   ALALSELEKGNIEGGRTSLWIRAWLQEQLFILGCFLQGDAGKVLFVAILVLSTFCVGLKS
       ** .. **.  *  ....  .*. .*  .  * ** .* . ** * *...*....* ****.
```

TABLE 1-continued alignment of human, mouse, fly, and butterfly PTC homologs

```
HPTC  ANLETNVEELWVEVGGRVSRELNYTRQKIGEEAMFNPQLMIQTPKEEGANVLTTEALLQH
MPTC  ANLETNVEELWVEVGGRVSRELNYTRQKIGEEAMFNPQLMIQTPKEEGANVLTTEALLQH
PTC   AQIHSKVHQLWIQEGGRLEAELAYTQKTIGEDESATHQLLIQTTHDPNASVLHPQALLAH
BPTC  AQIHTRVDQLWVQEGGRLEAELKYTAQALGEADSSTHQLVIQTAKDPDVSLLHPGALLEH
      *....  *..**..  ***.   ** **  . .**       **.***   .   ..*   *** *

HPTC  LDSALQASRVHVYMYNRQWKLEHLCYKSGELITET-GYMDQIIEYLYPCLIITPLDCFWE
MPTC  LDSALQASRVHVYMYNRQWKLEHLCYKSGELITET-GYMDQIIEYLYPCLIITPLDCFWE
PTC   LEVLVKATAVKVHLYDTEWGLRDMCNMPSTPSFEGIYYIEQILRHLIPCSIITPLDCFWE
BPTC  LKVVHAATRVTVHMYDIEWRLKDLCYSPSIPDFEGYHHIESIIDNVIPCAIITPLDCFWE
      *     *. * *  .*. .* *...    ..    *    ..  * .  ** ********

HPTC  GAKLQSGTAYLLGKPPLR----WTNFDPLEFLEELK------KINYQVDSWEEMLNKAEV
MPTC  GAKLQSGTAYLLGKPPLR----WTNFDPLEFLEELK------KINYQVDSWEEMLNKAEV
PTC   GSQLL-GPESAVVIPGLNQRLLWTTLNPASVMQYMKQKMSEEKISFDFETVEQYMKRAAI
BPTC  GSKLL-GPDYPIYVPHLKHKLQWTHLNPLEVVEEVK-KL---KFQFPLSTIEAYMKRAGI
      *..*  *    .   *  *     **  ..*    .*         *. .  *   ...*.

HPTC  GHGYMDRPCLNPADPDCPATAPNKNSTKPLKMALVLNGGCHGLSRKYMHWQEELIVGGTV
MPTC  GHGYMDRPCLNPADPDCPATAPNKNSTKPLDVALVLNGGCQGLSRKYMHWQEELIVGGTV
PTC   GSGYMEKPCLNPLNPNCPDTAPNKNSTQPPDVGAILSGGCYGYAAKHMHWPEELIVGGRK
BPTC  TSAYMKKPCLDPTDPHCPATAPNKKSGHIPDVAAELSHGCYGFAAAYMHWPEQLIVGGAT
      .**  .***.*  .*.** *****.*   *.. *. ** ***    *.*****

HPTC  KNSTGKLVSAHALQTMFQLMTPKQMYEHFKGYEYVSHINWNEDKAAAILEAWQRTYVEVV
MPTC  KNATGKLVSAHALQTMFQLMTPKQMYEHFRGYDYVSHINWNEDRAAAILEAWQRTYVEVV
PTC   RNRSGHLRKAQALQSVVQLMTEKEMYDQWQDNYKVHHLGWTQEKAAEVLNAWQRNFSREV
BPTC  RNSTSALRSARALQTVVQLMGEREMYEYWADHYKVHQIGWNQEKAAAVLDAWQRKFAAEV
      .*   ..  *  *.***..  ***    ..**.    .   *  ..  *  *.***   .    *

HPTC  HQSVAQNSTQK----VLSFTTTTLDDILKSFSDVSVIRVASGYLLMLAYACLTMLRW-DC
MPTC  HQSVAPNSTQK----VLPFTTTTLDDILKSFSDVSVIRVASGYLLMLAYACLTMLRW-DC
PTC   EQLLRKQSRIATNYDIYVFSSAALDDILAKFSHPSALSIVIGVAVTVLYAFCTLLRWRDP
BPTC  RKI-TTSGSVSSAYSFYPFSTSTLNDILGKFSEVSLKNIILGYMFMLIYVAVTLIQWRDP
      .    .          *....*.***  **. *     .  *    . *     *...* *

HPTC  SKSQGAVGLAGVLLVALSVAAGLGLCSLIGISFNAATTQVLPFLALGVGVDDVFLLAHAF
MPTC  SKSQGAVGLAGVLLVALSVAAGLGLCSLIGISFNAATTQVLPFLALGVGVDDVFLLAHAF
PTC   VRGQSSVGVAGVLLMCFSTAAGLGLSALLGIVFNASSTQVVPFLALGLGVDHIFMLTAAY
BPTC  IRSQAGVGIAGVLLLSITVAAGLGFCALLGIPFNASSTQIVPFLALGLGVQDMFLLTHTY
      ..*..**.*****..   *****  .*.**   ***..**.****** .**....*.*    ..

HPTC  SETGQNKRIPFEDRTGECLKRTGASVALTSISNVTAFFMAALIPIPALRAFSLQAAVVVV
MPTC  SETGQNKRIPFEDRTGECLKRTGASVALTSISNVTAFFMAALIPIPALRAFSLQAAVVVV
PTC   AESN------RREQTKLILKKVGPSILFSACSTAGSFFAAAFIPVPALKVFCLQAAIVMC
BPTC  VEQAGD--VPREERTGLVLKKSGLSVLLASLCNVMAFLAAALLPIPAFRVFCLQAAILLL
      *           ..*  **. * *. ...      .*. **..*.**..    * ****...

HPTC  FNFAMVLLIFPAILSMDLYRREDRRLDIFCCFTSPCVSRVIQVEPQAYTDTHDNTRYSPP
MPTC  FNFAMVLLIFPAILSMDLYRREDRRLDIFCCFTSPCVSRVIQVEPQAYTEPHSNTRYSPP
PTC   SNLAAALLVFPAMISLDLRRRTAGRADIFCCCF-PVWKEQPKVAPPVLPLNNNNGR----
BPTC  FNLGSILLVFPAMISLDLRRRSAARADLLCCLM-P---ESP------LPKKKIPER----
      *..  **.***..*.** **   * *...**   *       *

HPTC  PPYSSHSFAHETQITMQSTVQLRTEYDPHTHVYYTTAEPRSEISVQPVTVTQDT LSCQSP
MPTC  PPYTSHSFAHETHITMQSTVQLRTEYDPHTHVYYTTAEPRSEISVQPVTVTQDNLSCQSP
PTC   ----------------------------------GARHPKSCNNNRVPLPAQNPLLEQRA
BPTC  ----------------------------------AKTRKNDKTHRID-TTRQPLDPDVS
                                          .  ..  .    ... *  ..

HPTC  ESTSSTRDLLSQFSDSSLHCLEPPCTKWTLSSFAEKHYAPFLLKPKAKVVVIFLFLGLLG
MPTC  ESTSSTRDLLSQFSDSSLHCLEPPCTKWTLSSFAEKHYAPFLLKPKAKVVVILLFLGLLG
PTC   DIPGSS------------HSLASF----SLATFAFQHYTPFLMRSWVFLTVMGFLAALI
BPTC  ENVTKT------------CCL-SV----SLTKWAKNQYAPFIMRPAVKVTSMLALIAVIL
      .   .                *  .      .*.   *   ...*.**....  *    ....

HPTC  VSLYGTTRVRDGLDLTDIVPRETREYDFIAAQFKYFSFYNMYIVTQKA-DYPNIQHLLYD
MPTC  VSLYGTTRVRDGLDLTDIVPRETREYDFIAAQGKYFSFYNMYIVTQKA-DYPNIQHLLYD
PTC   SSLYASTRLQDGLDIIDLVPKDSNEHKFLDAQTRLFGFYSMYAVTQGNFEYPTQQQLLRD
BPTC  TSVWGATKVKDGLDLTDIVPENTDEHEFLSRQEKYFGFYNMYAVTQGNFEYPTNQKLLYE
      *.  ..*...****. *.** ..  *.    *  .*.**.**  ***   .**   * **  .

HPTC  LHRSFSNVKYVMLEENKQLPKMWLHYFRDWLQGLQDAFDSDWETGKIMPNN-YKNGSDDG
MPTC  LHKSFSNVKYVMLEENKQLPQMWLHYFRDWLQGLQDAFDSDWETGRIMPNN-YKNGSDDG
PTC   YHDSFVRVPHVIKNDNGGLPDFWLLLFSEWLGNLQKIFDEEYRDGRLTKECWFPNASSDA
BPTC  YHDQFVRIPNIIKNDNGGLTKFWLSLFRDWLLDLQVAFDKEVASGCITQEYWCKNASDEG
      *  *   .. ..   ..* *  ** **  .** ** **  . *.   *.* ..
```

TABLE 1-continued alignment of human, mouse, fly, and butterfly PTC homologs

```
HPTC    NIRPHRPEWVHDKADYMPETRLRIPAAEPIEYAQFPFYLNGLRDTSDFVEAIEKVRTICS
MPTC    NIRPHRPEWVHDKADYMPETRLRIPAAEPIEYAQFPFYLNGLRDTSDFVEAIEKVRVICN
PTC     KLYPEPRQYFHQPNEY----DLKIPKSLPLVYAQMPFYLHGLTDTSQIKTLIGHIRDLSV
BPTC    NLKPQPQRWIHSPEDV----HLEIKKSSPLIYTQLPFYLSGLSDTDSIKTLIRSVRDLCL
        .. *.       *    .      * *  . *. *.* **** ** **   .  .* .

HPTC    NYTSLGLSSYPNGYPFLFWEQYIGLRHWLLLFISVVLACTFLVCAVFLLNPWTAGIIVMV
MPTC    NYTSLGLSSYPNGYPFLFWEQYISLRHWLLLSISVVLACTFLVCAVFLLNPWTAGIIVMV
PTC     KYEGFGLPNYPSGIPFIFWEQYMTLRSSLAMILACVLLAALVLVSLLLLSVWAAVLVILS
BPTC    KYEAKGLPNFPSGIPFLFWEQYLYLRTSLLLALACALGAVFIAVMVLLLNAWAAVLVTLA
        .* . **...*.* **.*****. **   *  ...   *   ..  ..**. *.* .. .

HPTC    LALMTVELFGMMGLIGIKLSAVPVVILIASVGIGVEFTVHVALAFLTAIGDKNRRAVLAL
MPTC    LALMTVELFGMMGLIGIKLSAVPVVILIASVGIGVEFTVHVALAFLTAIGDKNHRAMLAL
PTC     VLASLAQIFGAMTLLGIKLSAIPAVILILSVGMMLCFNVLISLGFMTSVGNRQRRVQLSM
BPTC    LATLVLQLLGVMALLGVKLSAMPPVLLVLAIGRGVHFTVHLCLGFVTSIGCKRRRASLAL
        .    ...* * *.*.****.* ***. ..*  . * * . *.*.*..*  .  .*  *...

HPTC    EHMFAPVLDGAVSTLLGVLMLAGSEFDFIVRYFFAVLAILTILGVLNGLVLLPVLLSFFG
MPTC    EHMFAPVLDGAVSTLLGVLMLAGSEFDFIVRYFFAVLAILTVLGVLNGLVLLPVLLSFFG
PTC     QMSLGPLVHGMLTSGVAVFMLSTSPFEFVIRHFCWLLLVVLCVGACNSLLVFPILLSMVG
BPTC    ESVLAPVVHGALAAALAASMLAASEFGFVARLFLRLLLALVFLGLIDGLLFFPIVLSILG
        .  ...*....*   ...  ..  **. * * *.  * *   .*   .*   ...*. .*...** *

HPTC    PYPEVSPANGLNRLPTPSPEPPPSVVRFAMPPGHTHSGSDSSDSEYSSQTTVSGLSE-EL
MPTC    PCPEVSPANGLNRLPTPSPEPPPSVVRFAVPPGHTNNGSDSSDSEYSSQTTVSGISE-EL
PTC     PEAELVPLEHPDRISTPSPLPVRSSKRSGKSYVVQGSRSSRGSCQKSHHHHHKDLNDPSL
BPTC    PAAEVRPIEHPERLSTPSPKCSPIHPRKSSSSSGGGDKSSRTS--KSAPRPC----APSL
        *  .*. *  . .*..****          *...      *        *           *

HPTC    RHYEAQQGAGGPAHQVIVEATENPVFAHSTVVHPESRHHPPSNPRQQPHLDSGSLPPGRQ
MPTC    RQYEAQQGAGGPAHQVIVEATENPVFARSTVVHPDSRHQPPLTPRQQPHLDSGSLSPGRQ
PTC     TTITEEPQSWKSSNSSIQMPNDWTYQPREQ--RPASYAAPPPAYHKAAAQQHHQHQGPPT
BPTC    TTITEEPSSWHSSAHSVQSSMQSIVVQPEVVVETTTYNGSDSASGRSTPTKSSHGGAITT
                . .  ..   .      .          .   .

HPTC    GQQPRRDPPREGLWPPLYRPRRDAFEISTEGHSGPSNRARWGPRGARSHNPRNPASTAMG
MPTC    GQQPRRDPPREGLRPPPYRPRRDAFEISTEGHSGPSNRDRSGPRGARSHNPRNPTSTAMG
PTC     TPPPPFPTA-----------------YPPELQSIVVQPEVTVETTHS-----------DS
BPTC    TKVTATANIKVEVVTPSDRKSRRSYHYYDRRRDRDEDRDRDRERDRDRDRDRDRDRDRDR
                                      .  .

HPTC    SSVPGYCQPITTVTASASVTVAVHPPPVPGPGRNPRGGLCPGY---PETDHGLFEDPHVP
MPTC    SSVPSYCQPITTVTASASVTVAVHPP--PGPGRNPRGGPCPGYESYPETDHGVFEDPHVP
PTC     NT--------TKVTATANIKVELAMP-----GRAVRS---YNFTS---------------
BPTC    DR--------DRERSRERDRRDRYRD-----ERDHRA---SPRENGRDSGHE--------
                                               *  *.

HPTC    FHVRCERRDSKVEVIELQDVECEERPRGSSSN
MPTC    FHVRCERRDSKVEVIELQDVECEERPWGSSSN
PTC     --------------------------------
BPTC    -------------------------SDSSRH
```

The identity of ten other clones recovered from the mouse library is not determined. These cDNAs cross-hybridize with mouse ptc sequence, while differing as to their restriction maps. These genes encode a family of proteins related to the patched protein. Alignment of the human and mouse nucleotide sequences, which includes coding and noncoding sequence, reveals 89% identity.

Radiation hybrid mapping of the human ptc gene. Oligonucleotide primers and conditions for specifically amplifying a portion of the human ptc gene from genomic DNA by the polymerase chain reaction were developed. This marker was designated STS SHGC-8725. It generates an amplification product of 196 bp, which is observed by agarose gel electrophoresis when human DNA is used as a template, but not when rodent DNA is used. Samples were scored in duplicate for the presence or absence of the 196 bp product in 83 radiation hybrid DNA samples from the Stanford G3 Radiation Hybrid Panel (purchased from Research Genetics, Inc.) By comparison of the pattern of G3 panel scores for those with a series of Genethon meiotic linkage markers, it was determined that the human ptc gene had a two point lod score of 1,000 with the meiotic marker D9S287, based on no radiation breaks being observed between the gene and the marker in 83 hybrid cell lines. These results indicate that the ptc gene lies within 50–100 kb of the marker. Subsequent physical mapping in YAC and BAC clones confirmed this close linkage estimate. Detailed map information can be obtained from http://www.shgc.stanford.edu.

Analysis of BCNS mutations. The basal cell nevus syndrome has been mapped to the same region of chromosome 9q as was found for ptc. An initial screen of EcoRI digested DNA from probands of 84 BCNS kindreds did not reveal major rearrangements of the ptc gene, and so screening was performed for more subtle sequence abnormalities. Using vectorette PCR, by the method according to Riley et al. (1990) *N.A.R.* 18:2887–2890, on a BAC that contains genomic DNA for the entire coding region of ptc, the intronic sequence flanking 20 of the 24 exons was determined. Single strand conformational polymorphism analysis of PCR-amplified DNA from normal individuals, BCNS patients and sporadic basal cell carcinomas (BCC) was performed for 20 exons of ptc coding sequence. The amplified samples giving abnormal bands on SSCP were then sequenced.

In blood cell DNA from BCNS individuals, four independent sequence changes were found; two in exon 15 and two in exon 10. One 49 year old man was found to have a sequence change in exon 15. His affected sister and daughter have the same alteration, but three unafflicted relatives do not. His blood cell DNA has an insertion of 9 base pairs at nucleotide 2445 of the coding sequence, resulting in the insertion of three amino acids (PNI) after amino acid 815. Because the normal sequence preceding the insertion is also PNI, a direct repeat has been formed.

The second case of an exon 15 change is an 18 year old woman who developed jaw cysts at age 9 and BCCs at age 6. The developmental effects together with the BCCs indicate that she has BCNS, although none of her relatives are known to have the syndrome. Her blood cell DNA has a deletion of 11 bp, removing the sequence ATATCCAGCAC at nucleotides 2441 to 2452 of the coding sequence. In addition, nucleotide 2452 is changed from a T to an A. The deletion results in a frameshift that is predicted to truncate the protein after amino acid 813 with the addition of 9 amino acids. The predicted mutant protein is truncated after the seventh transmembrane domain. In Drosophila, a ptc protein that is truncated after the sixth transmembrane domain is inactive when ectopically expressed, in contrast to the full-length protein, suggesting that the human protein is inactivated by the exon 15 sequence change. The patient with this mutation is the first affected family member, since her parents, age 48 and 50, have neither BCCs nor other signs of the BCNS. DNA from both parents' genes have the normal nucleotide sequence for exon 15, indicating that the alteration in exon 15 arose in the same generation as did the BCNS phenotype. Hence her disease is the result of a new mutation. This sequence change is not detected in 84 control chromosomes.

Analysis of sporadic basal cell carcinomas. To determine whether ptc is also involved in BCCs that are not associated with the BCNS or germline changes, DNA was examined from 12 sporadic BCCs. Three alterations were found in these tumors. In one tumor, a C to T transition in exon 3 at nucleotide 523 of the coding sequence changes a highly conserved leucine to phenylalanine at residue 175 in the first putative extracellular loop domain. Blood cell DNA from the same individual does not have the alteration, suggesting that it arose somatically in the tumor. SSCP was used to examine exon 3 DNA from 60 individuals who do not have BCNS, and found no changes from the normal sequence. Two other sporadic BCCs have deletions encompassing exon 9 but not extending to exon 8.

The existence of sporadic and hereditary forms of BCCs is reminiscent of the characteristics of the two forms of retinoblastoma. This parallel, and the frequent deletion in tumors of the copy of chromosome 9q predicted by linkage to carry the wild-type allele, demonstrates that the human ptc is a tumor suppressor gene. PTC represses a variety of genes, including growth factors, during Drosophila development and may have the same effect in human skin. The often reported large body size of BCNS patients also could be due to reduced ptc function, perhaps due to loss of control of growth factors. The C to T transition identified in ptc in the sporadic BCC is also a common genetic change in the p53 gene in BCC and is consistent with the role of sunlight in causing these tumors. By contrast, the inherited deletion and insertion mutations identified in BCNS patients, as expected, are not those characteristic of ultraviolet mutagenesis.

The identification of the ptc mutations as a cause of BCNS links a large body of developmental genetic information to this important human disease. In embryos lacking ptc function part of each body segment is transformed into an anterior-posterior mirror-image duplication of another part. The patterning changes in ptc mutants are due in part to derepression of another segment polarity gene, wingless, a homolog of the vertebrate Wnt genes that encodes secreted signaling proteins. In normal embryonic development, ptc repression of wg is relieved by the Hh signaling protein, which emanates from adjacent cells in the posterior part of each segment. The resulting localized wg expression in each segment primordium organizes the pattern of bristles on the surface of the animal. The ptc gene inactivates its own transcription, while Hh signaling induces ptc transcription.

In flies two other proteins work together with Hh to activate target genes: the ser/thr kinase fused and the zinc finger protein encoded by *cubitus interruptus*. Negative regulators working together with ptc to repress targets are protein kinase A and costal2. Thus, mutations that inactivate human versions of protein kinase A or costal2, or that cause excessive activity of human hh, gli, or a fused homolog, may modify the BCNS phenotype and be important in tumorigenesis.

In accordance with the subject invention, mammalian patched genes, including the mouse and human genes, are provided, which can serve many purposes. Mutations in the gene are found in patients with basal cell nevus syndrome, and in sporadic basal cell carcinomas. The autosomal dominant inheritance of BCNS indicates that patched is a tumor suppressor gene. The patched protein may be used in a screening for agonists and antagonists, and for assaying for the transcription of ptc mRNA. The protein or fragments thereof may be used to produce antibodies specific for the protein or specific epitopes of the protein. In addition, the gene may be employed for investigating embryonic development, by screening fetal tissue, preparing transgenic animals to serve as models, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for assessing a genetic predisposition of an animal for a skin cancer, the method comprising:
   detecting, from a sample of nucleic acid isolated from the animal, a loss-of-function mutation in a patched gene in the germline of said animal,
   wherein the presence of said loss-of-function mutation indicates that said animal has a genetic predisposition for basal cell carcinoma.

2. The method according to claim 1, wherein said sample of nucleic acid is from a biopsy of cells isolated from the animal.

3. The assay of claim 1, wherein the cell sample is obtained from a human patient.

4. The assay of claim 3, wherein the cell sample is obtained from a biopsy.

5. The assay of claim 3, wherein the biopsy is obtained from a carcinoma, meningiomoa, medulloma or fibroma.

6. A method for determining a patched phenotype of cells of a tumor comprising detecting, from a sample of nucleic acid isolated from the cells, the presence or absence of a loss-of-function mutation of a patched gene in the cells.

7. The method according to claim 6, wherein the tumor is a carcinoma.

8. The method according to claim 7, wherien said carcinoma is a basal cell carcinoma.

9. The method according to claim 6, wherein said nucleic acid is from a biopsy of cells of said tumor.

10. An assay for determining the patched phenotype of a cell, comprising
    providing a nucleic acid sample isolated from mammalian cells,
    detecting the presence or absence of a patched gene sequence or allelic variant thereof, by hybridization of the nucleic acid sample with one or more nucleic acid probes which hybridize to a mammalian patched gene.

11. The assay of claim 10, wherein hybridization of the probe(s) further comprises subjecting the probe(s) and nucleic acid sample to an amplification process and detecting abnormalities in an amplified product.

12. The assay of claim 11, wherein the amplification process is polymerase chain reaction (PCR).

13. The assay of claim 10, wherein the probe(s) hybridizes to SEQ ID No. 9 or 18 under stringency conditions equivalent to 10×SCC at 50° C. to SEQ ID No. 9 or 18.

14. The assay of claim 10, wherein the probe(s) hybridizes to SEQ ID No. 9 or 18 under stringency conditions equivalent to 5×SSC at 60° C.

15. The assay of claim 10, wherein the probe(s) hybridizes to SEQ ID No. 9 or 18 under stringency conditions equivalent to 0.1×SCC at 60° C.

16. The assay of claim 10, wherein the probe(s) further comprises a label group attached to the nucleic acid and able to be detected.

17. The assay of claim 10, wherein the probe(s) are at least 15 nucleotides in length.

18. The assay of claim 10, wherein the probe(s) are at least 50 nucleotides in length.

19. The assay of claim 10, wherein the probe(s) are 15–100 nucleotides in length.

20. The method of claim 10, wherein the nucleic acid sample is an mRNA sample from the mammalian cells.

21. The method of claim 10, wherein the nucleic acid sample is a cDNA sample reverse transcribed from mRNA of the mammalian cells.

22. The method of claim 10, wherein the nucleic acid sample is genomic DNA from the mammalian cells.

23. The method of claim 10, which method detects loss of heterozygosity in a patched gene of the mammalian cells.

24. The assay of claim 10, wherein the sequence of the detected patched is determined.

25. The assay of claim 24, wherein the presence or absence of a deletion of one or more nucleotides from the patched gene, an addition of one or more nucleotides to the patched gene, or a substitution of one or more nucleotides of the patched gene is determined from the sequence.

26. An assay for detecting mutations of a patched gene, comprising detecting, in a sample of isolated mammalian cells or nucleic acid isolated therefrom, the presence or absence of a deletion of one or more nucleotides from the patched gene, an addition of one or more nucleotides to the patched gene, a substitution of one or more nucleotides of the patched gene, a chromosomal rearrangement of all or a portion of the patched gene, an alteration in the level of an mRNA transcript of the patched gene, or alteration of the splicing pattern of an mRNA transcript of the patched gene.

27. The assay of claim 26, wherein all or a portion of the patched gene is amplified by an amplification process and abnormalities in an amplified product, if any, are detected.

28. The assay of claim 27, wherein the amplification process is polymerase chain reaction (PCR).

29. The assay of claim 26, wherein mutations of the patched gene are detected by single strand conformational polymorphism analysis.

30. The assay of claim 26, wherein mutations of the patched gene are detected by gel electrophoresis.

31. The assay of claim 26, wherein mutations of the patched gene are detected by digestions with one or more endonucleases.

32. An assay for phenotyping the patched status of a cell, comprising detecting, in a sample of isolated mammalian cells, the presence or absence of a genetic lesion of a patched gene characterized by at least one of (i) aberrant mutation of a patched gene resulting in loss of function, and (ii) misexpression of the patched gene resulting in loss of function.

33. The assay of claim 32, which assay includes:
    i. providing one or more nucleic acid probes comprising a region of nucleotide sequence which hybridizes to a sense or antisense sequence of the patched gene, or naturally occurring mutants thereof;

ii. combining the probe(s) with a nucleic acid sample from the cells; and iii. detecting, by hybridization of the probe(s) to the nucleic acid, the presence or absence of a deletion of one or more nucleotides from the patched gene, an addition of one or more nucleotides to the patched gene, a substitution of one or more nucleotides of the patched gene, a chromosomal rearrangement of all or a portion of the patched gene, an alteration in the level of an mRNA transcript of the patched gene, or alteration of the splicing pattern of an mRNA transcript of the patched gene.

34. The assay of claim 33, wherein the probe(s) hybridizes to a sequence designated by SEQ ID No. 9 or 18 under stringency conditions equivalent to 10×SSC at 50° C.

35. The assay of claim 33, wherein the probe(s) hybridizes to a sequence designated by SEQ ID No. 9 or 18 under stringency conditions equivalent to 5×SSC at 50° C.

36. The assay of claim 33, wherein the probe further comprises a label group attached to the nucleic acid and able to be detected.

37. The assay of claim 33, wherein all or a portion of the patched gene is amplified by an amplification process and abnormalities in an amplified product, if any, are detected.

38. The assay of claim 37, wherein the amplification process is polymerase chain reaction (PCR).

39. The assay of claim 32, wherein mutations of the patched gene are detected by single strand conformational polymorphism analysis.

40. The assay of claim 32, wherein mutations of the patched gene are detected by gel electrophoresis.

41. The assay of claim 32, wherein mutations of the patched gene are detected by digestions with one or more endonucleases.

42. The assay claim 32, wherein detecting the lesion comprises ascertaining, relative to a wild-type level of hedgehog-dependent patched signal transduction, the ability of cells in cell sample to respond to hedgehog induction.

43. A method for assessing a genetic predisposition of an animal for developing basal cell nevus syndrome, the method comprising:

detecting, from a sample of nucleic acid isolated from the animal, a loss-of-function mutation in a patched gene in the germline of said animal, wherein the presence of said loss-of-function mutation indicates that said animal has a genetic predisposition for developing basal cell nevus syndrome.

44. The method according to claim 43, wherein said sample of nucleic acid is from a biopsy of cells isolated from the animal.

* * * * *

UNITED STATES PATENT AND TRADEMARK OFFICE
CERTIFICATE OF CORRECTION

PATENT NO : 6,027,882
DATED : February 22, 2000
INVENTOR(S): Matthew P. Scott, et. al.

It is certified that error appears in the above-identified patent and that said Letters Patent is hereby corrected as shown below:

Please make the following addition to [73] Assignee:

--Board of Trustees of the Leland Stanford Junior University--

Signed and Sealed this

Twenty-fourth Day of April, 2001

Attest:

NICHOLAS P. GODICI

Attesting Officer

Acting Director of the United States Patent and Trademark Office